United States Patent
Terada

(10) Patent No.: US 9,386,992 B2
(45) Date of Patent: Jul. 12, 2016

(54) LIGATION DEVICE AND CLIP UNIT USED THEREIN

(71) Applicant: FUJIFILM Corporation, Tokyo (JP)

(72) Inventor: Kazuhiro Terada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 675 days.

(21) Appl. No.: 13/848,074

(22) Filed: Mar. 21, 2013

(65) Prior Publication Data

US 2013/0211432 A1    Aug. 15, 2013

Related U.S. Application Data

(63) Continuation of application No. PCT/JP2011/060994, filed on May 15, 2011.

(30) Foreign Application Priority Data

Sep. 22, 2010  (JP) ................................ 2010-212892

(51) Int. Cl.
*A61B 17/122* (2006.01)
*A61B 17/128* (2006.01)
*A61B 17/29* (2006.01)

(52) U.S. Cl.
CPC ........... *A61B 17/122* (2013.01); *A61B 17/1285* (2013.01); *A61B 2017/2908* (2013.01)

(58) Field of Classification Search
CPC ........... A61B 17/1227; A61B 17/1222; A61B 17/128; A61B 17/1285
See application file for complete search history.

(56) References Cited

U.S. PATENT DOCUMENTS

| 6,139,563 A | 10/2000 | Cosgrove, III et al. |
| 2002/0151916 A1 | 10/2002 | Muramatsu et al. |
| 2008/0140089 A1 | 6/2008 | Kogiso et al. |
| 2009/0228023 A1* | 9/2009 | Cui .................... A61B 17/1285 606/142 |

FOREIGN PATENT DOCUMENTS

| JP | 2001-505810 A | 5/2001 |
| JP | 2006-198388 A | 8/2006 |
| JP | 2007-507307 A | 3/2007 |
| JP | 2007-275445 A | 10/2007 |
| JP | 2008-119526 A | 5/2008 |
| JP | 2010-337 A | 1/2010 |
| WO | WO 2005/032381 A2 | 4/2005 |

OTHER PUBLICATIONS

Form PCT/ISA/210 mailed Jun. 7, 2011 for International Application No. PCT/JP2011/060994.

* cited by examiner

*Primary Examiner* — Katherine Rodjom
(74) *Attorney, Agent, or Firm* — Birch, Stewart, Kolasch & Birch, LLP

(57) ABSTRACT

Each of the clip units 13 includes a clip body 35 having a pair of arm parts 41 that can ligate the biological tissue and a fastening ring 37 that accommodates the clip body 35, and the plurality of clip units 13 are disposed in series within the distal end of the outer sheath member 19. Each of the fastening rings 37 includes a connecting mechanism 85 consisted by a locking member 87 that connects the adjacent fastening rings 37 each other and a fitting support 101, the manipulation wire 23 engaged with the locking member 87 is pulled to release the connection of the fastening rings 37 by the connecting mechanism 87.

8 Claims, 29 Drawing Sheets

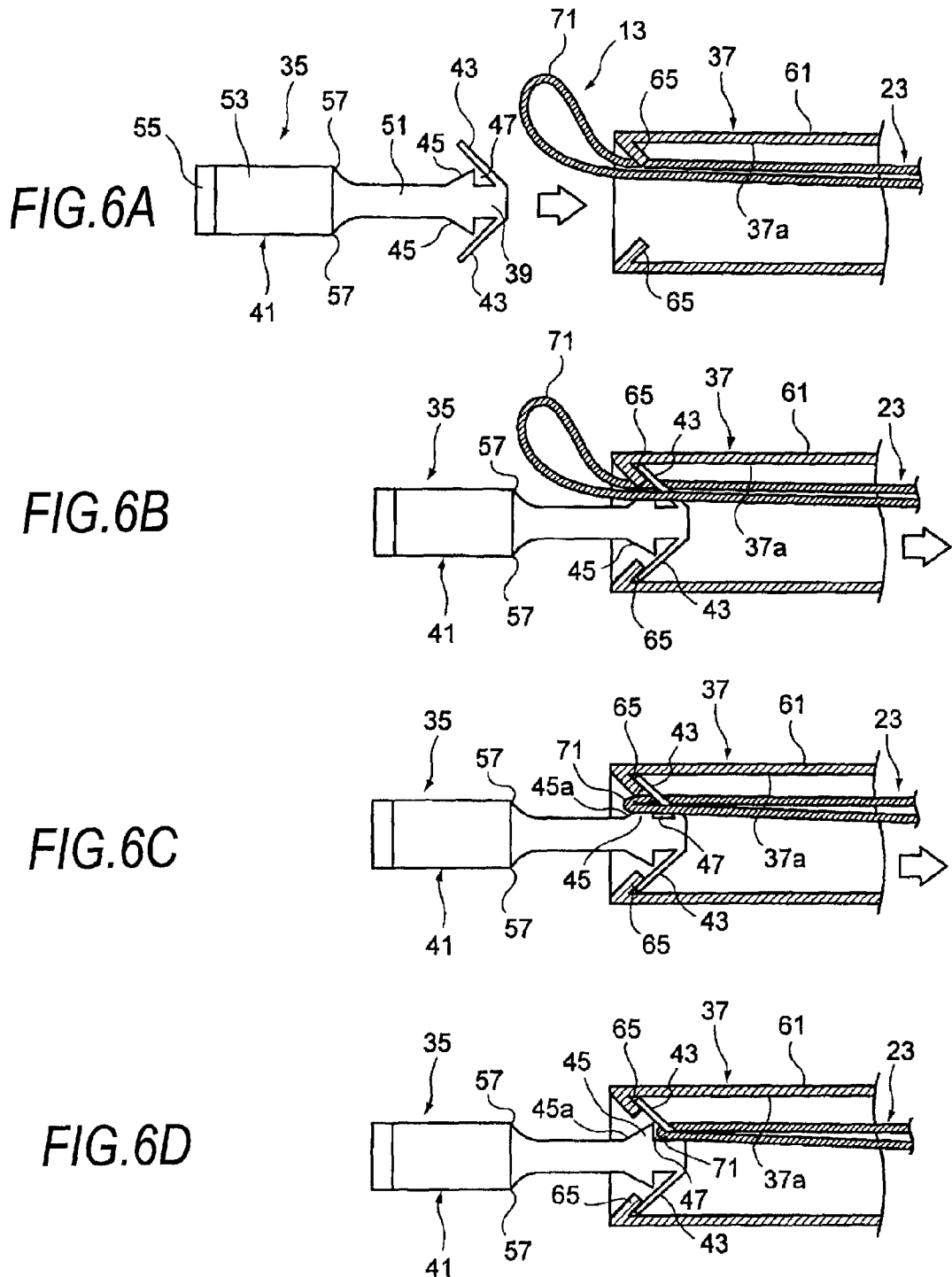

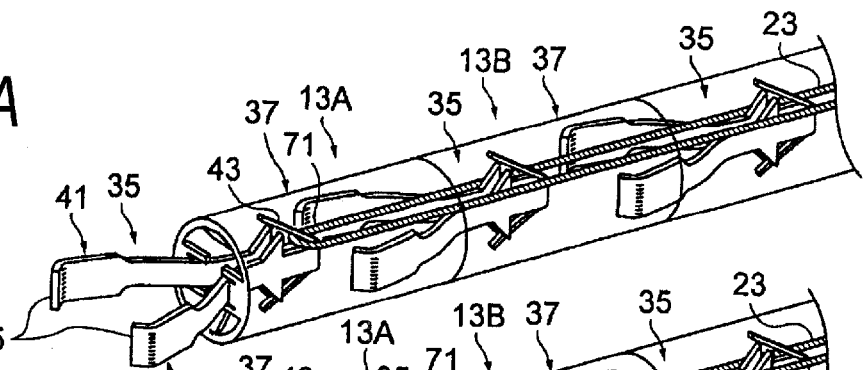
FIG.10A
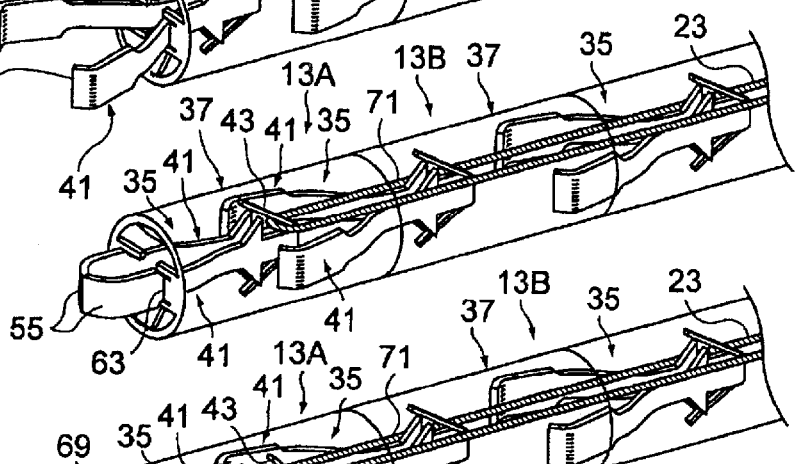
FIG.10B
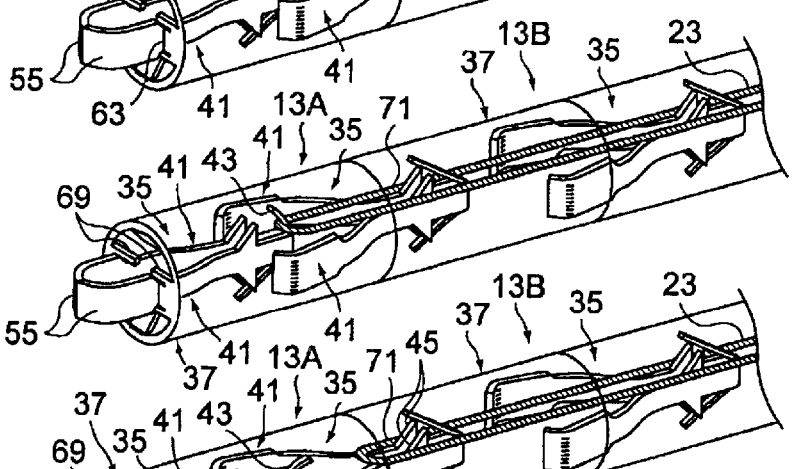
FIG.10C
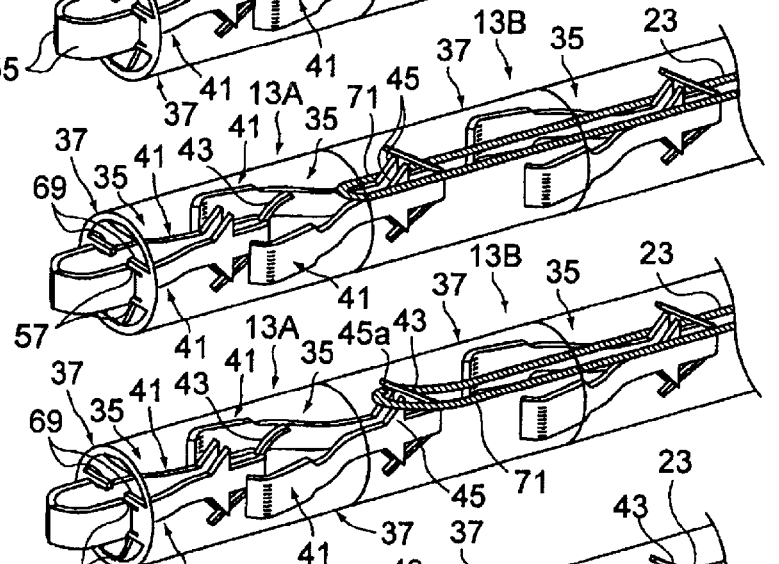
FIG.10D
FIG.10E
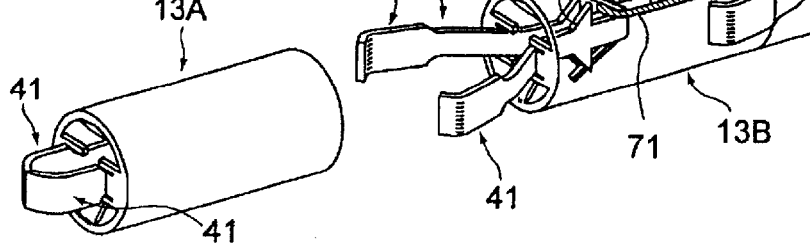
FIG.10F

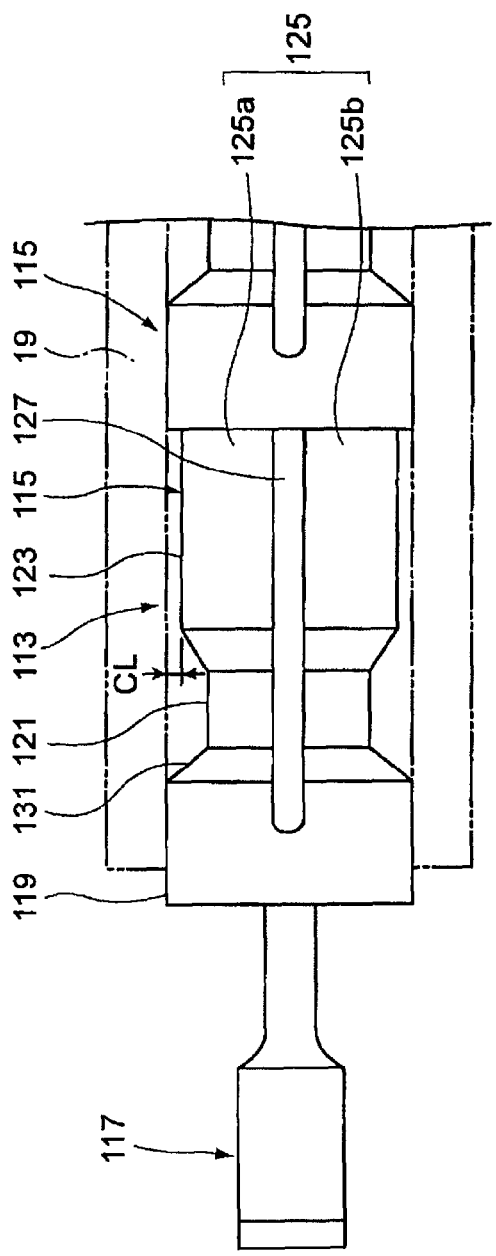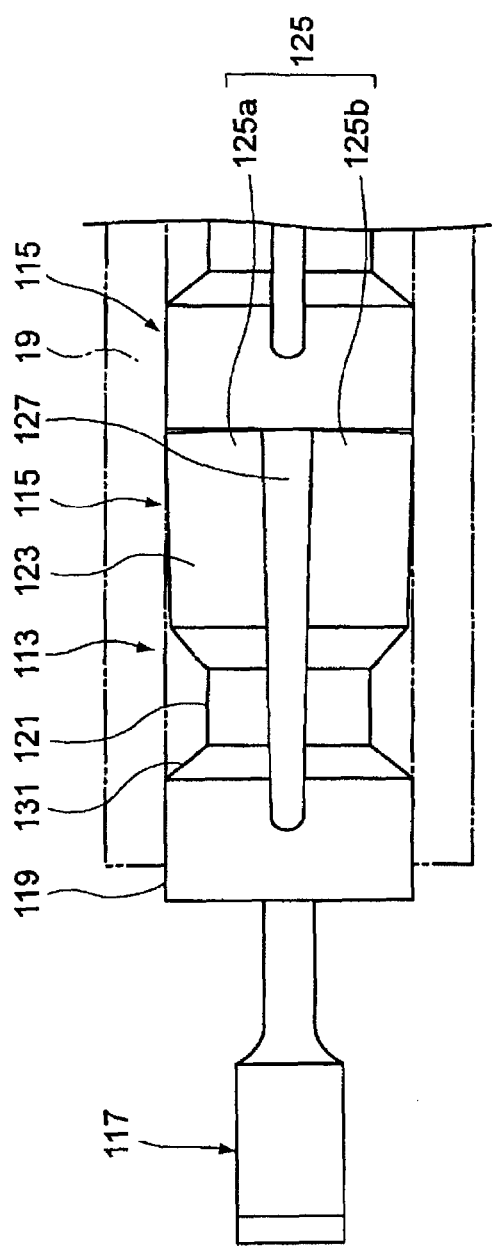

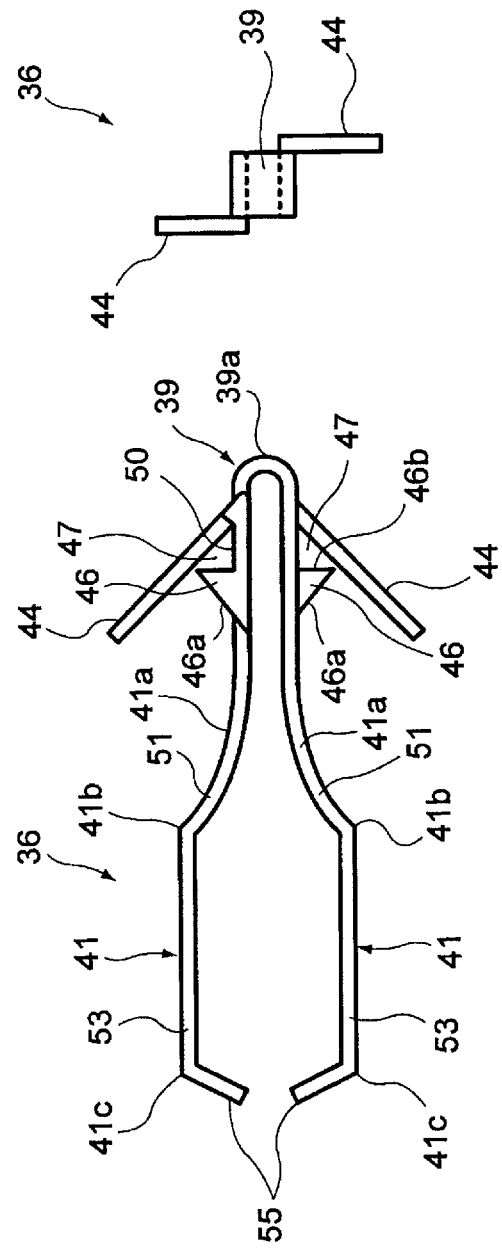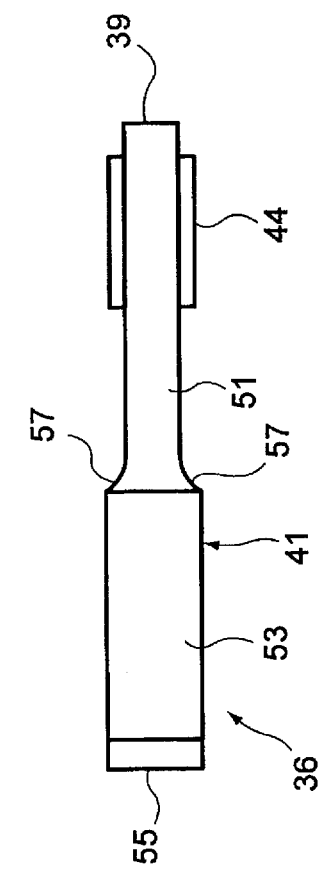
FIG.30A
FIG.30B
FIG.30C

LIGATION DEVICE AND CLIP UNIT USED THEREIN

CROSS REFERENCE TO RELATED APPLICATIONS

This application is a Continuation of PCT International Application No. PCT/JP2011/060994 filed on May 12, 2011, which claims priority under 35 U.S.C. §119(a) to Patent Application No. 2010-212892 filed in Japan on Sep. 22, 2010, all of which are hereby expressly incorporated by reference into the present application.

TECHNICAL FIELD

The present invention relates to a ligation device that ligates a biological tissue and a clip unit used therein.

BACKGROUND ART

As a ligation device to ligate a biological tissue, for example, it has been known that a ligation device is inserted into a body cavity from a forceps port of an endoscope into a body cavity, a manipulation wire connected to a clip is pull-manipulated so as to fit the clip of which an arm part of the front end is enlarged and opened to a position of the desired biological tissue, and the arm part of the clip is closed to ligate the biological tissue (see, e.g., Patent Literatures 1 and 2).

The ligation devices for the biological tissue disclosed in Patent Literatures 1 and 2 are configured to include an introducing pipe inserted into the body cavity, the manipulation wire inserted within the introducing pipe to be freely reciprocated, and the clip connected to the manipulation wire and loaded in a front end part of the introducing pipe. The ligation devices have a structure in which the clip is detained in the body cavity in a state where the clip grips the biological tissue by pulling the manipulation wire. However, the ligation device in Patent Literature 1 forces a fitting part to be widened to be released by passage of a bulging body, but there is a concern that the deformation of the fitting part is small and the fitting is not released.

In the ligation device in Patent Literature 2, a clip constituted by a clip claw member and a pressing member is temporarily fixed to a front end of a sheath, and thus the clip claw member can be manipulated at either of an opened state and a closed state. However, since the clip is separated from the manipulation wire by fracture of a semi-circular part that connects to the clip and the manipulation wire, there is a concern that a small piece of fragment may be generated when the semi-circular part is broken. The fragment may enter into the introducing pipe of the ligation device or be detained within the body cavity. When the fragment is detained within the body cavity, there is a concern that it may cause a trouble to the manipulation of the manipulation wire that is continuously performed and sequential ligations of the biological tissues by a clip at the next step will not be performed. Therefore, it is not appropriate to a structure used for a repeating ligation device. Also, it is not preferable to detain the fragment within the body cavity inadvertently.

CITATION LIST

Patent Literature

Patent Literature 1    JP-A-2007-507307
Patent Literature 2    JP-A-2006-198388

SUMMARY OF INVENTION

Technical Problem

An object of the present invention is to provide a ligation device and a clip unit used therein in which, while arm parts of a clip body disposed in a front end of a sheath, among a plurality of clip units disposed in series with the sheath, may be freely opened/closed to grip a biological tissue, biological tissues may be sequentially ligated by the plurality of clip units without generating a fragment.

Solution to Problem

The present invention is made by the following configuration.

A ligation device for ligating a biological tissue, includes: a flexible tube-shaped outer sheath member; a tube-shaped inner sheath member provided within the outer sheath member to be freely reciprocated; a manipulation wire provided within the sheath member to be freely reciprocated; and a plurality of clip units disposed in series within the distal end of the outer sheath member, in which each of the clip units includes a clip body that ligates the biological tissue using a pair of arm parts biased to be largely opened each other and a base end section that connects the base ends of the arm parts, and a fastening ring configured to close the pair of arm parts by inserting the base end section of the clip body within a cylindrical body of the fastening ring, and in which the fastening ring includes: a connecting unit to connect adjacent fastening rings to each other; and a disconnection unit to engage with the manipulation and deforms the connecting unit by the pull of the manipulation wire, thereby releasing the connection of the fastening rings.

Advantageous Effects of Invention

With the ligation device and the clip unit used therein according to the present invention, while arm parts of the clip body disposed in the front end of the sheath may be freely opened/closed to grip a biological tissue among a plurality of clip units disposed in series within the sheath, biological tissues may be sequentially ligated by the plurality of clip units without generating the fragment.

BRIEF DESCRIPTION OF DRAWINGS

FIG. 6A is a cross-sectional view of a main part of the clip body, a fastening ring and a manipulation wire prior to assembling, FIG. 6B is a cross-sectional view of a main part when the clip body is inserted into the fastening ring, FIG. 6C is a cross-sectional view of a main part during engaging the manipulation wire with a wire engagement unit of the clip body, and FIG. 6D is a cross-sectional view of a main part illustrating a state where a loop part of the manipulation wire is engaged with the wire engagement unit of the clip body.

FIG. 10A is a perspective view of the ligation device prior to ligation, FIG. 10B is a perspective view illustrating a state where the arm parts of the clip body pulled by the manipulation wire and disposed in the front end is closed, FIG. 10C is a perspective view illustrating a state where the engagement claw of the clip body in the front end begins to be plastically deformed, FIG. 10D is a perspective view illustrating a state where the engagement claw is plastically deformed to release the engagement of the clip body and the loop part, FIG. 10E is a perspective view illustrating a state where the loop part is guided by a disengagement part of the next clip body and introduced to the wire engagement unit, and FIG. 10F is a perspective view illustrating a state where the loop part of the manipulation wire is engaged with the wire engagement unit of the next clip body and the clip unit in the front end is separated.

FIG. 23A is a side view illustrating an appearance in FIG. 20, and FIG. 23B is a side view illustrating an appearance in FIG. 22.

FIG. 30A is a plan view, FIG. 30B is a front view, and FIG. 30C is a side view of the clip body in FIG. 29.

DESCRIPTION OF EMBODIMENTS

Hereinafter, exemplary embodiments of the present invention will be described with reference to the accompanying drawings.

Figure 1:
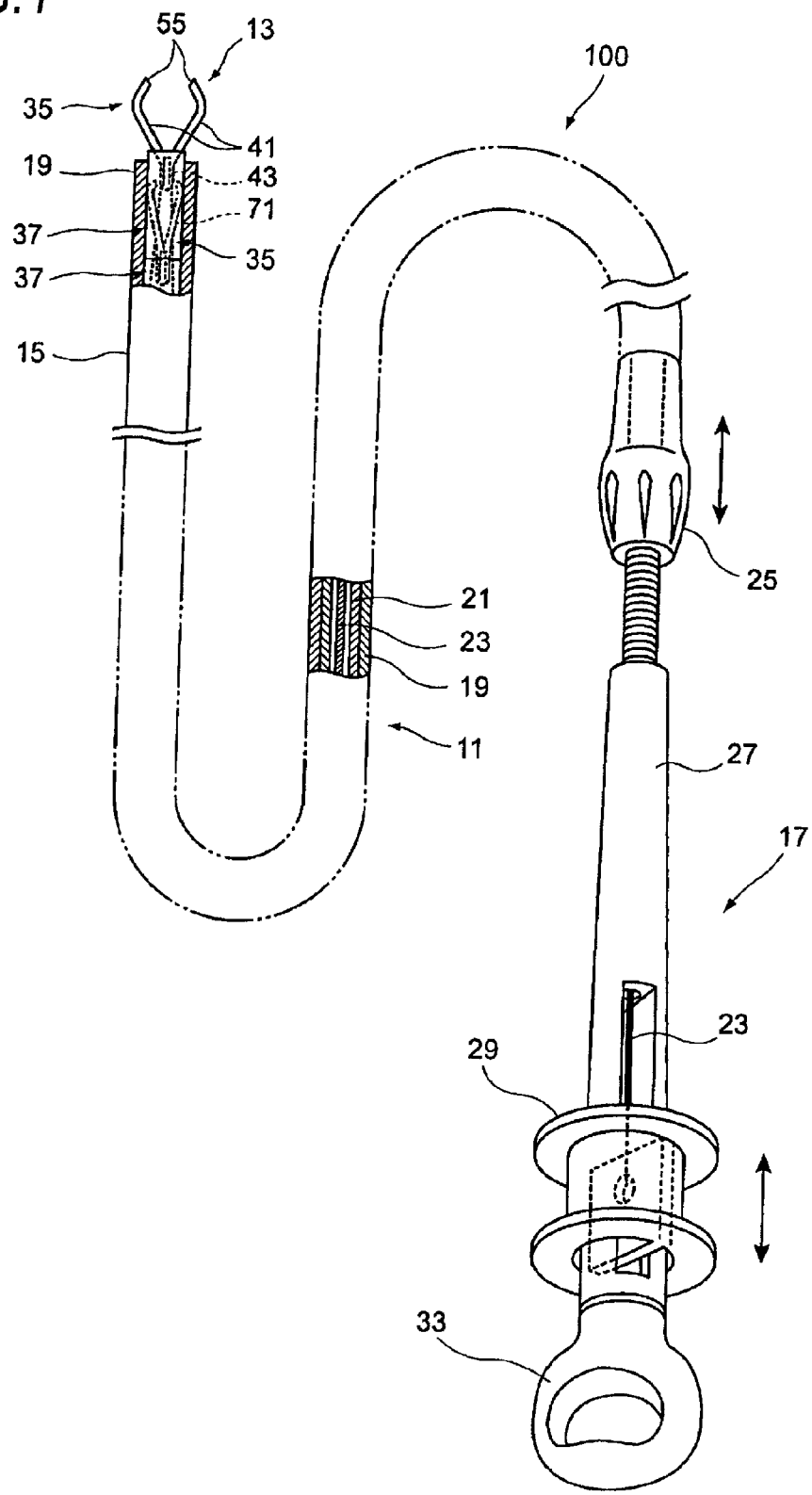
FIG. 1 is an entire configuration view illustrating a ligation device of which a portion is cut-off as a view for describing an exemplary embodiment of the present invention.
Figure 2:
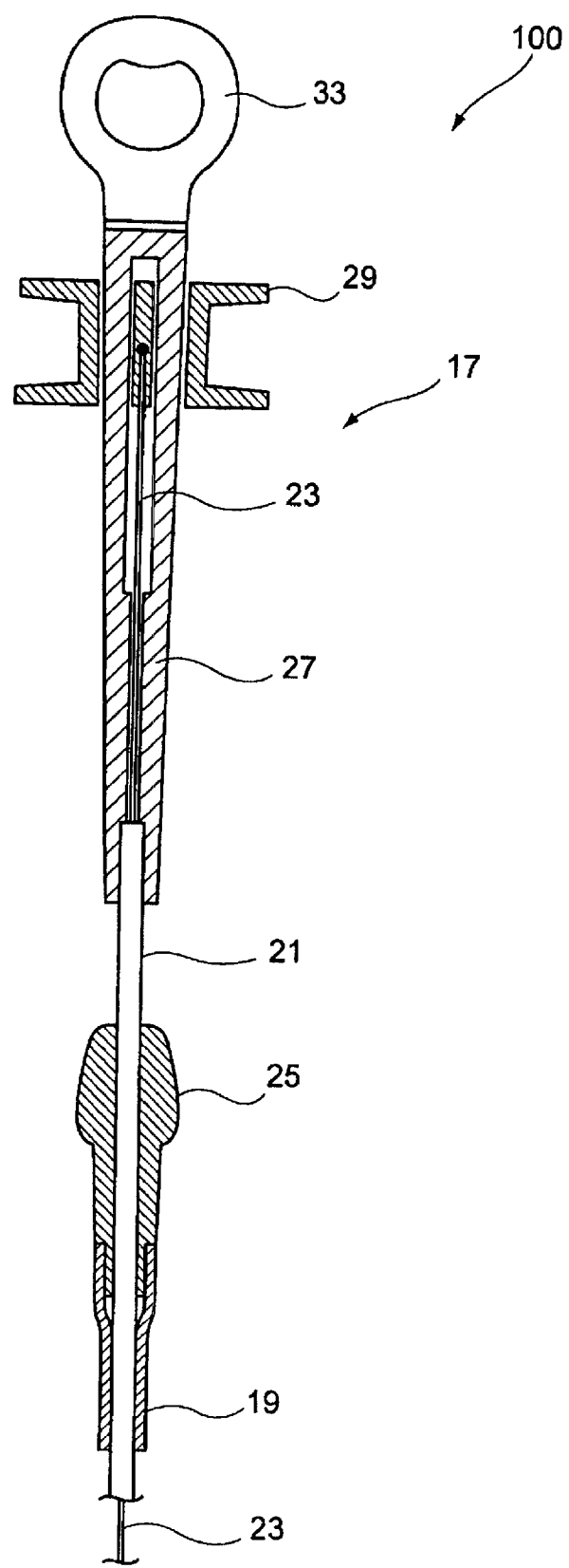
FIG. 2 is a cross-sectional view of a handle manipulation unit of the ligation device illustrated in FIG. 1.

FIG. 1 is an entire configuration view illustrating a ligation device of which a portion is cut-off as a view for describing an exemplary embodiment of the present invention, and FIG. 2 is a cross-sectional view of a handle manipulating unit.

A ligation device 100 includes a clip manipulation device 11 and a clip unit 13 which is loaded in the clip manipulation device 11. The clip manipulation device 11 includes an insertion part 15 to be inserted into a channel of an endoscope (not shown) to be inserted into a body cavity, and a handle manipulation unit 17 located at the base end side of the insertion part 15. The insertion part 15 includes an outer sheath member 19 which is an introducing pipe made of, for example, high-density polyethylene tube, an inner sheath member 21 which is inserted through the outer sheath member 19 to be freely reciprocated, and a manipulation wire 23 which is inserted through the inner sheath member 21 to be freely reciprocated.

The inner sheath member 21 is constituted by a coil sheath having flexibility made by densely winding a linear element having elastic resilience. The manipulation wire 23 is formed of metallic stranded wire having a appropriate elasticity, for example, a stainless steel and a NiTi alloy. As necessary, the outer peripheral thereof may be covered with high-density polyethylene or may be coated with silicon oil so as to improve slideable mobility with the inner sheath member 21. The front end of the manipulation wire 23, at a distal end side which is opposite to the handle manipulation unit 17 side, is provided with an annular loop part 71.

The clip unit 13 includes a fastening ring 37 formed as a cylindrical body and a clip body 35 inserted into the cylindrical body of the fastening ring 37. Plural of clip units 13 are disposed along the axis direction from the distal end of the outer sheath member 19. In a clip unit at the terminal, which is opposite to the distal end, among the plural of clip units 13, the rear end of the fastening ring 37, which is opposite to the insertion side of the clip body 35, abuts on the front end surface of the distal end of the inner sheath member 21.

The handle manipulation unit 17 includes: an outer sheath-connection body 25 to fix the base end side of the outer sheath member 19; a manipulation unit body 27 to fix the base end side of the inner sheath member 21; a slider 29 disposed to be freely reciprocated to the manipulation unit body 27 and connected to the manipulation wire 23; and a finger pull ring 33 connected to the manipulation unit body 27. The handle manipulation unit 17 adjusts the relative position between the outer sheath member 19 and the inner sheath member 21 by relatively moving the outer sheath-connection body 25 and the manipulation unit body 27. Further, by relatively moving the manipulation unit body 27 and the slider 29, the relational position between the clip unit 13 connected to the manipulation wire 23 and the inner sheath member 21.

The clip manipulation device 11 is configured such that, when the manipulation unit body 27 is pressed in a state where the outer sheath-connection body 25 is fixed, the outer sheath member 19 is moved to the rear side relative to the inner sheath member 21 at the distal end, and, when the manipulation unit body 27 is pulled to the rear side, the outer sheath member 19 is moved to the front side relative to the inner sheath member 21 at the distal end. Further, when the slider 29 is moved in a direction which is spaced apart from the finger pull ring 33, the manipulation wire 23 is moved in a direction where the manipulation wire 23 protrudes from the inner sheath member 21, and, when the slider 29 is moved to be close to the finger pull ring 33, the manipulation wire 23 is moved in a direction where the manipulation wire 23 is pulled into the inner sheath member 21. The clip unit 13 loaded in the distal end of the outer sheath member 19 is maintained by the manipulation wire 23, and leaves out of the clip manipulation device 11 by the pulling of the manipulation wire 23, which will be described later.

<Clip Unit>

Next, the configuration of the clip unit 13 will be described in detail.

Figure 3:
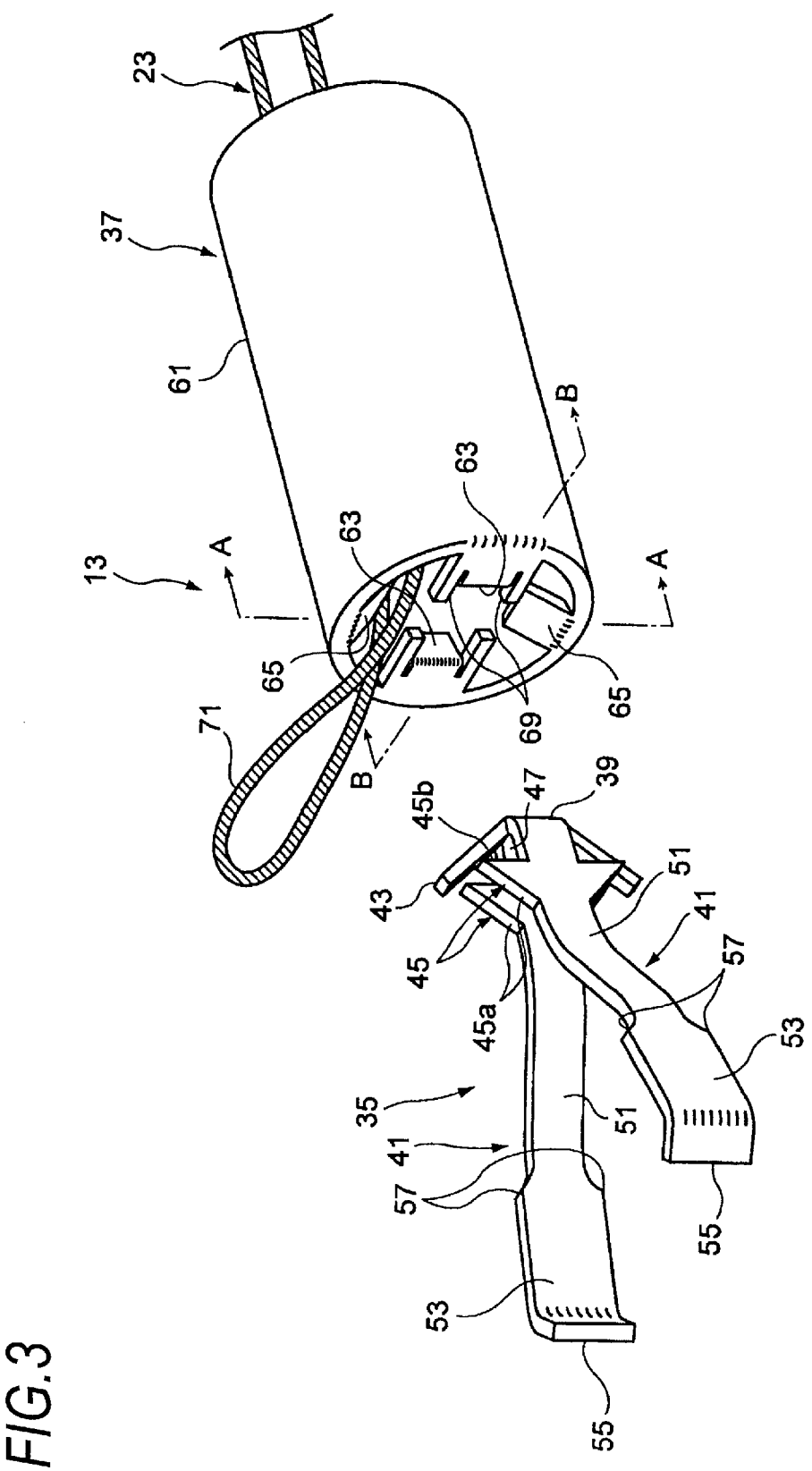
FIG. 3 is an exploded perspective view of the clip unit illustrated in FIG. 1.

An exploded perspective view of a clip unit is illustrated in FIG. 3. The clip unit 13 includes a fastening ring 37 and a clip body 35 that is inserted into a cylindrical body of the fastening ring 37. The clip body 35 includes: a pair of arm parts 41 which are expanded and biased in relation to each other; and a base end section 39 that interconnects the base ends of the arm parts 41. The clip body 35 strongly grips a biological tissue by the arm parts 41. The clip body 35 is formed by bending a band-shaped resilient metallic plate material in a substantial U-shape, which has a elastic resilience. The metallic plate material such as a stainless steel. The fastening ring 37 is a cylindrical member made out of a metallic material such as a stainless steel, and the manipulation wire 23 is inserted through the inside of the fastening ring 37. The base end side of the clip body 35 is accommodated within the fastening ring 37 in a state where the loop part 71 of the manipulation wire 23 is engaged with a part of the clip body 35.

<Clip Body>

Figure 4A:
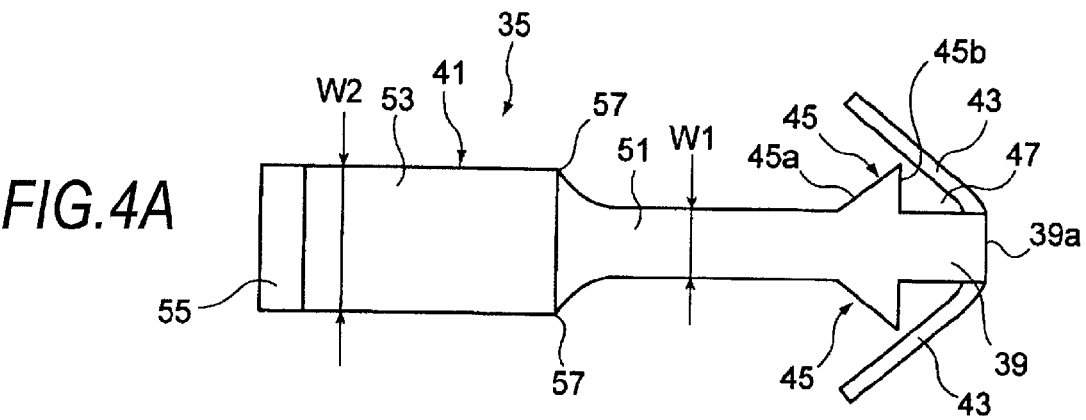
FIGS. 4A and 4B are a side view and a plan view of the clip body illustrated in FIG. 3, respectively.
Figure 4B:
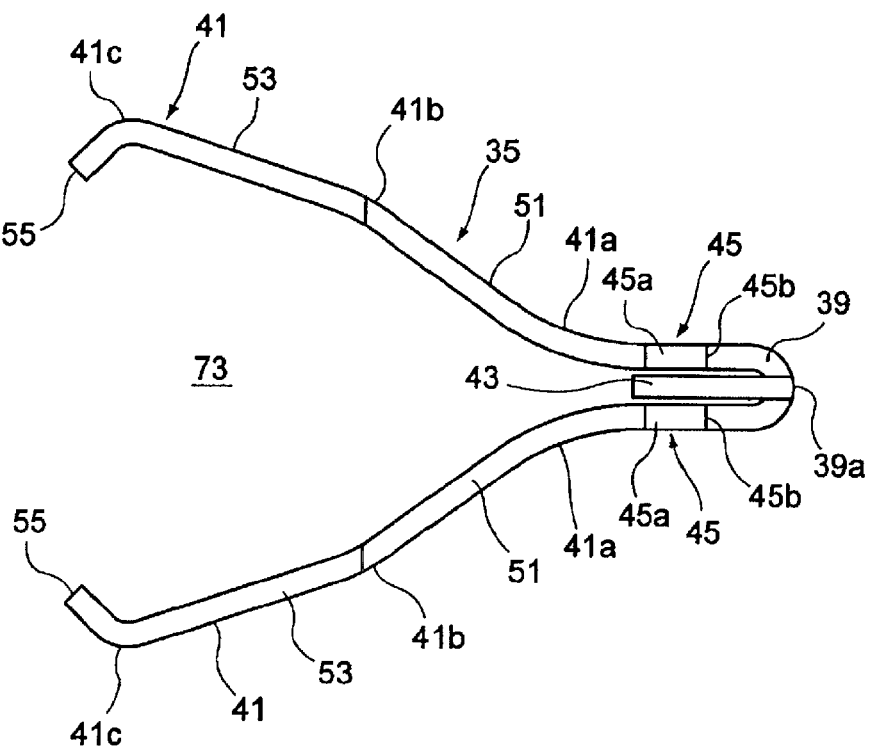

The clip body 35 has a shape which is illustrated in FIG. 4A as a side view of the clip body and FIG. 4B as a plan view thereof. The clip body 35 includes a wire engaging unit constituted by engagement claws 43 and disengagement prevention parts 45 at the base end section 39 thereof. The wire engagement unit engages the loop part 71 of the manipulation wire 23. The engagement claws 43 are configured to be extended and widened outside toward the arm parts 41 from the both side in the width direction of the arm parts 41 at the bottom part 39a of the base end section 39. That is, the engagement claws 43 are configured to be extended and inclined to the outside in a radial direction of the fastening ring 37, toward the opposite direction to the insertion direction to the fastening ring 37 from the base end section 39 of the clip body 35. The engagement claws 43 are plate-shaped bodies of which widths are narrow such that a force to plastically deform the engagement claws 43 is larger than a force to pull the clip body 35 into the fastening ring 37.

Each of the disengagement prevention part 45 is a protrusion which protrudes toward the engagement claw 43 from a position spaced from a connection position with the engagement claw 43 at the base end section 39 of the clip unit 35, and has a inclined surface 45a of which protrusion height toward the engagement claw 43 gradually increases toward the insertion direction to the fastening ring 37 of the clip body 35. Accordingly, a gap 47 that engages the loop part 71 of the manipulation wire 23 is defined by the engagement claw 43, the side surface 45b at the base end section 39 side of the disengagement prevention part 45 and a width direction-side surface of the base end section 39. The gap between the protruding front end of the disengagement prevention part 45 and the engagement claw 43 is configured to be smaller than the diameter of the manipulation wire 23, and, when the loop part 71 of the manipulation wire 23 elastically deforms the engagement claw 43 to enter into the gap 47, prevent the loop part 71 of the manipulation wire 23 from being leaved from the gap 47, which will be described in detail later.

Meanwhile, in the illustrated example, the engagement claws 43 and the disengagement prevention parts 45 are formed in a pair of top and bottom sides, but they may be formed in either one side. Further, as in the illustrated example, the engagement claws 43 and the disengagement prevention parts 45 are formed in a pair of top and bottom sides, and at the same time, two loop parts 71 of the manipulation wires 23 may be formed and each of the loop parts 71 is separately engaged with one of the pair of top and bottom engagement claws 43, respectively. At that case, the pulling force of the manipulation wire 23 can move the clip body 35 stably without biasing.

The pair of arm parts 41 are formed by band-shaped resilient metallic plate-shaped members which are symmetrically arranged to be opposed to each other, and each of the arm parts 41 includes: a plate-shaped member 51 having a predetermined width in a direction perpendicular to the enlarged opening direction of the pair of arm parts 41; a wide width part 53 of which the width is wider than the plate-shaped member 51; and a tissue gripping part 55 in which a biological tissue can be interposed therebetween. The pair of arm parts 41 are biased to be enlarged and opened from each other by the elastic resilience which the material of the clip body 35 has. As such, the pair of arm parts 41 are provided with wide width parts 53 of which the width are gradually wider from the plate-shaped members 51, step parts 57 formed between the wide width parts 53 and the plate-shaped members 51, and tissue griping parts 55 formed at the front end side of the wide width parts 53, which will be described in detail as follows.

The pair of arm parts 41 are outwardly bent to be enlarged and opened from first bending points 41a formed at the base end section 39 side of the plate-shaped member 51 and are inwardly bent from second bending points 41b formed in the middle position of the plate-shaped member 51. In addition, the arm parts 41 are inwardly bent from third bending points 64c at the front end side of the wide width parts 53, thereby forming the tissue gripping parts 55.

When the pair of arm parts 41 are opened by the elastic resilience of the clip body 35, the pair of tissue gripping parts 55 are largely spaced from each other, thereby forming a grasping gap 73 between the tissue gripping parts 55. When the pair of arm parts 41 are closed, the front ends may be contacted to each other, thereby gripping the biological tissue. Meanwhile, the front ends of the tissue gripping parts 55 may be straight type as illustrated in the drawings, or may be formed in a concave-convex shape that are interlocked to each other such that a biological tissue may be certainly interposed therebetween.

<Fastening Ring>

Figure 5A:
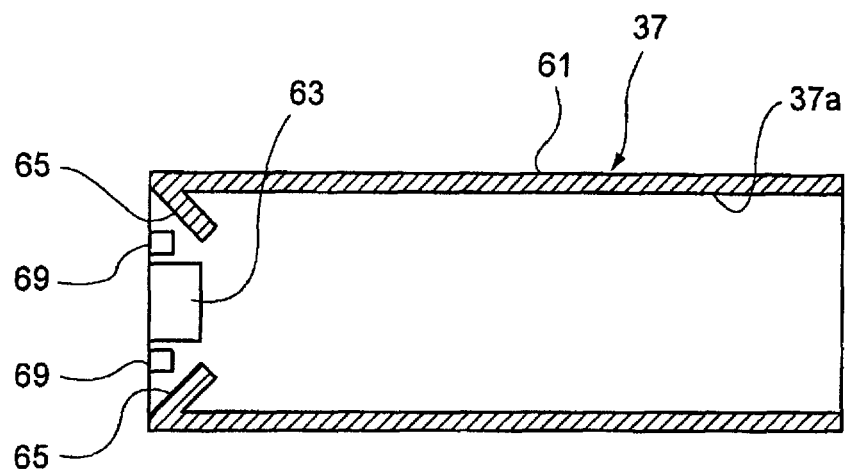
FIGS. 5A and 5B are a cross-sectional view taken along line A-A in FIG. 3 and a cross-sectional view taken along line B-B in FIG. 3, respectively.
Figure 5B:
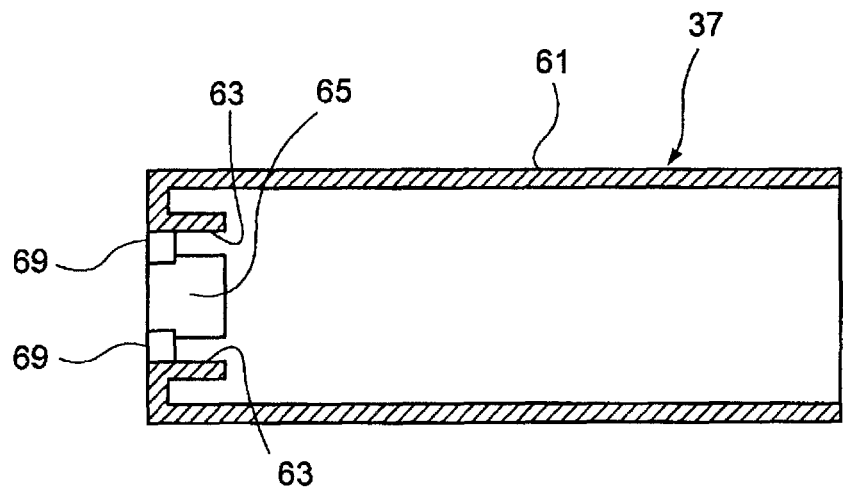

FIGS. 5A and 5B are a cross-sectional view taken along line A-A in FIG. 3 and a cross-sectional view taken along line B-B in FIG. 3, respectively. As illustrated in FIGS. 3, 5A and 5B, the fastening ring 37 includes a hollow cylindrical part 61, a pair of clip contact parts 63, and a pair of clip disengagement prevention members 65.

The fastening ring 37 closes the pair of arm parts 41 of the clip body 35 by inserting the base end section 39 of the clip body 35 into the cylindrical body. The pair of clip contact parts 63 and the pair of clip disengagement prevention parts 65 are formed by bending a pair of protrusions inwardly in the diameter direction of the fastening ring 37. The protrusions are formed by being protruded to the axis direction from an end of the cylindrical part 61. The clip disengagement prevention members 65 are formed to be extended and inclined to inner side of the ring toward the insertion direction of the clip body 35 from the end of the fastening ring 37 at the clip body inserting side. The pair of clip contact parts 63 are disposed in different circumference positions from each other by 180 degrees, the pair of clip disengagement prevention members 65 are disposed in different circumference positions from each other by 180 degrees, and a clip contact part 63 and a clip disengagement prevention member 65 are disposed in different circumference positions by 90 degrees.

The pair of clip contact parts 63 have flat surfaces parallel to the axis of the fastening ring 37 by bending the protrusions protruded from an end part of the cylindrical part 61. In both sides of the clip contact parts 63 are provided with a pair of guide members 69 that protrude inwardly in the diameter direction of the fastening ring 37. The interval of the pair of guide members 69 is set to a width larger than a width W1 of the plate-shaped member 51 of the clip body 35 (see, FIGS. 4A and 4B) and smaller than a width W2 of the wide width part 53.

Therefore, when the clip body 35 is inserted into the fastening ring 37, the flat surfaces of the clip contact parts 63 contact the both outer surfaces of the arm parts 41 to guide the clip body 35, thereby restricting the rotation of the clip body 35 with reference to the center axis of the fastening ring 37. At the same time, the step part 57 between the wide width part 53 and the plate-shaped member 51 contacts to the pair of guide members 69 to restrict the insertion length of the clip body 35 into the fastening ring 37.

In addition, when the clip body 35 is inserted into the fastening ring 37 from the base end section 39 side, the both outer surfaces of the pair of arm parts 41 are biased by the flat surface of the clip contact part 63 to close the arm parts 41. A flat surface of the clip contact part 63 formed by contacting the both outer surfaces of the arm parts 41 is not specifically limited thereto as long as the flat surface may restrict the rotation of the clip body 35 with respect to the central axis of the fastening ring 37. For example, a plurality of protrusions that point contact to the both outer surfaces or a protrusion that linearly contact to the both outer surfaces may be used.

The pair of clip disengagement prevention members 65 are formed at an end portion of the cylindrical part 61, and is inclined to the front of the insertion direction of the clip body 35 and inwardly in the diameter direction of the fastening ring 37 from the end of the fastening ring 37 at the clip body insertion side to be extended with a substantial V shaped cross-section. The pair of clip disengagement prevention members 65 are engaged with the engagement claws 43 of the clip body 35 (see, FIG. 3) inserted to the fastening ring 37, thereby preventing the clip body 35 inserted once from being disengaged from the fastening ring 37.

<Connection Between Clip Unit and Manipulation Wire>

The clip body 35 and the fastening ring 37, as described above, form a clip unit 13 by inserting the clip unit 35 into the fastening ring 37. Then, plural of clip units 13 are loaded within the outer sheath member 19 of the clip manipulation device 11 (see, FIG. 1), and a leading clip unit 13 is engaged by the manipulation wire 23. FIGS. 6A to 6D illustrate an assembling sequence of the leading clip unit 13 into the clip manipulation device 11. Meanwhile, the clip manipulation device is omitted in the figures.

First, as illustrated in FIG. 6A, the loop part 71 formed in the front end of the manipulation wire 23 is inserted through the fastening ring 37, and the engagement claws 43 of the clip body 35 is passed through the inside of the loop part 71 of the manipulation wire 23. At that state, as illustrated in FIG. 6B, the clip body 35 is inserted into the fastening ring 37 from the base end section 39 side. By doing so, the engagement claws 43 contact to the pair of disengagement prevention members 65 to be resiliently deformed inwardly in the diameter direction of the fastening ring 37, thereby climbing over the disengagement prevention members 65. When the pair of engagement claws 43 pass the clip disengagement members 65, the engagement claws 43 are returned resiliently by the spring force, and the front end parts of the engagement claws 43 are connected to the inner peripheral surfaces 37a of the fastening ring 37. Therefore, the engagement claws 43 are engaged with the clip disengagement prevention members 65 at the inner side thereof, thereby preventing being disengaged from the fastening ring 37. In the ligation device according to the present invention, a plurality of clip units 13 are loaded in series within the outer sheath member 19, which will be described in detail later.

Here, as illustrated in FIG. 6C, when the manipulation wire 23 is pulled in a insertion direction of the clip body 35 (right direction in the figure), the loop part 71 is guided by the disengagement prevention members 65 of the fastening ring 37 and the disengagement prevention part 45 of the clip body 35 to be connected to the inner surface of the engagement claws 43. Then, as illustrated in FIG. 6D, the engagement claws 43 are resiliently deformed outwardly in a diameter direction of the fastening ring 37, and thus, the loop part 71 of the manipulation wire 23 is inserted into a gap 47 defined by the engagement claw 43, the disengagement prevention part 45, and the width direction-end surface of the base end section 39. Therefore, the manipulation wire 23 is engaged with the engagement claws 43.

Since the loop part 71 of the manipulation wire 23 is inserted into the gap 47 by the resilient deformation of the engagement claws 43, when the loop part 71 is inserted into the gap 47 once, the loop part 71 is not disengaged from the gap 47 as long as the engagement claws 43 are not deformed. As a result, the clip unit 13 is assembled into the clip manipulation device 11. Meanwhile, the manipulation wire 23 is engaged with a single side of the clip body 35 (upper side in the figure) in the illustrated example, but two lines of manipulation wires 23 may be engaged with the both sides of the clip body 35 (upper and lower sides in the figure).

<Basic Ligation Sequence by Ligation Device>

Figure 7A:
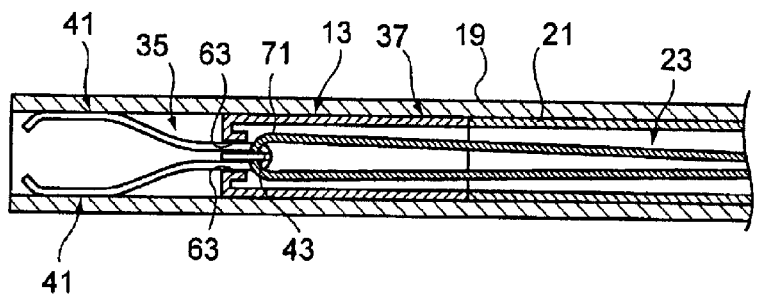
FIG. 7A is a cross-sectional view of a main part of the clip unit mounted within the introducing pipe.

The clip unit 13 assembled into the clip manipulation device 11 as described above is accommodated in the front end part of the distal side of the outer sheath member 19 by bringing up the outer sheath member 19 which is a introducing pipe to the front area, as illustrated in FIG. 7A. This is a state where the outer sheath connection body 25 illustrated in FIG. 1 is fixed in a place spaced from the manipulation unit main body 27. At this time, the base end side of the clip unit 13 contacts to the front end of the distal side of the inner sheath member 21. Further, the pair of arm parts 41 of the clip body 35 are contacted to the inner peripheral surface of the outer sheath member 19 brought up, and accommodated within the outer sheath member 19 in a state where the arm parts are resiliently deformed in a direction where the arm parts approach to each other. In a state where the outer side of the clip unit 13 is covered with the outer sheath member 19, the insertion part 15 of the ligation device 100 is inserted into a body cavity from a forceps hole of the endoscope (not illustrated) inserted into the body cavity in advance. Then, the front end of the insertion part 15 is guided up to the a portion to be ligated of a tissue while monitoring the inside of the body cavity by the endoscope.

Figure 7B:
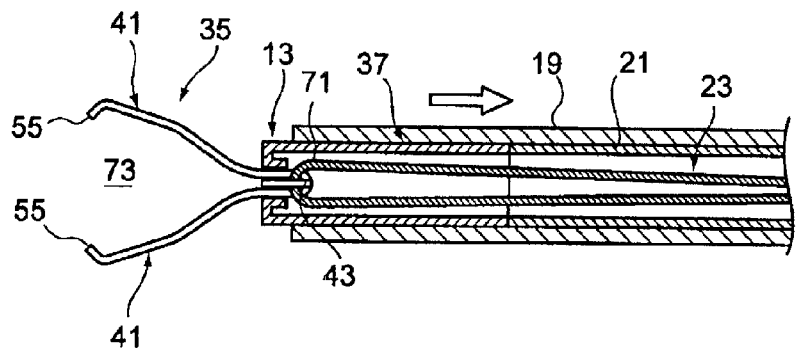
FIG. 7B is a cross-sectional view of a main part illustrating a state where the arm parts of the clip unit are opened by retracting the introducing pipe.

Next, when the outer sheath connection body 25 illustrated in FIG. 1 is moved up to a position where a leading clip is exposed and toward the manipulation unit main body 27 side and fixed, the clip unit 13 is biased by the inner sheath member 21 moving relatively within the outer sheath member 19 is moved to the front side (distal end side), thereby protruding the pair of arm parts 41 of the clip body 35 from the outer sheath member 19, as illustrated in FIG. 7B. Since the pair of arm parts 41 are opened from the restriction by the outer sheath member 19, the arm parts are largely opened by the spring force of the clip body 35 to form a narrowed gap 73 between the tissue gripping parts 55, 55. In this state, the clip body 35 is positioned such that a desired biological tissue is disposed in the narrowed gap 73.

Figure 7C:
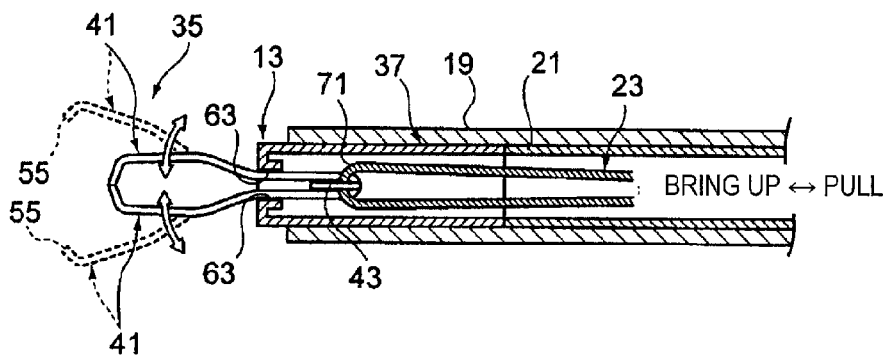
FIG. 7C is a cross-sectional view of a main part illustrating a state where the arm parts of the clip body are opened/closed by a bringing-up manipulation and a pulling manipulation of the manipulation wire.

In a state where position of the tissue gripping parts is optimized, the slider 29 illustrated in FIG. 1 is moved in a direction where the slider is close to the finger pull ring 33 to pull the manipulation wire 23 into the inner sheath member 21. Therefore, the manipulation wire 23 is relatively pulled with respect to the inner sheath. As illustrated in FIG. 7C, the loop part 71 of the manipulation wire 23 pulls the engagement claw 43 to pull the clip body 35 into the fastening ring 37. At this time, the pair of arm parts 41 contacting to flat surfaces of the clip contact parts 63 are closed by the clip contact parts 63 as illustrated in a solid line in the figure.

Further, when the slider 29 illustrated in FIG. 1 is moved to a direction where the slider is spaced away from the finger pull ring 33 to bring up the manipulation wire 23 with respect to the inner sheath relatively, the clip body 35 are pushed from the fastening ring 37 and the restriction of the pair of arm parts 41 by the flat surfaces of the clip contact parts 63 are released. Therefore, the pair of arm parts 41 are largely opened as illustrated in a broken line in the figure.

That is, when the manipulation wire 23 is relatively pulled with respect to the inner sheath, the pair of arm parts 41 are closed, and when the manipulation wire 23 is relatively brought up with respect to the inner sheath, the pair of arm parts 41 are opened. Meanwhile, during the manipulations as described above, since the both outer surfaces of the arm parts 41 are connected to the flat surfaces of the clip contact parts 63, the clip body 35 is advanced and retracted from the fastening ring 37 without rotating itself about the central axis of the fastening ring 37, thereby being stably opened/closed.

By the close and open operations as described above, the biological tissue may be grasped by a simple manipulation. That is, it may be grasped only by the manipulations of the manipulation part main body 27 and the finger pull ring 33, and thus, the manipulation of an operator may be performed briefly.

<Repeating Configuration of Clip Unit>

A plurality of clip units each having the above configuration are loaded in series within the outer sheath member. Hereinafter, the interrelation of the plurality of clip units will be described in detail.

Figure 8A:
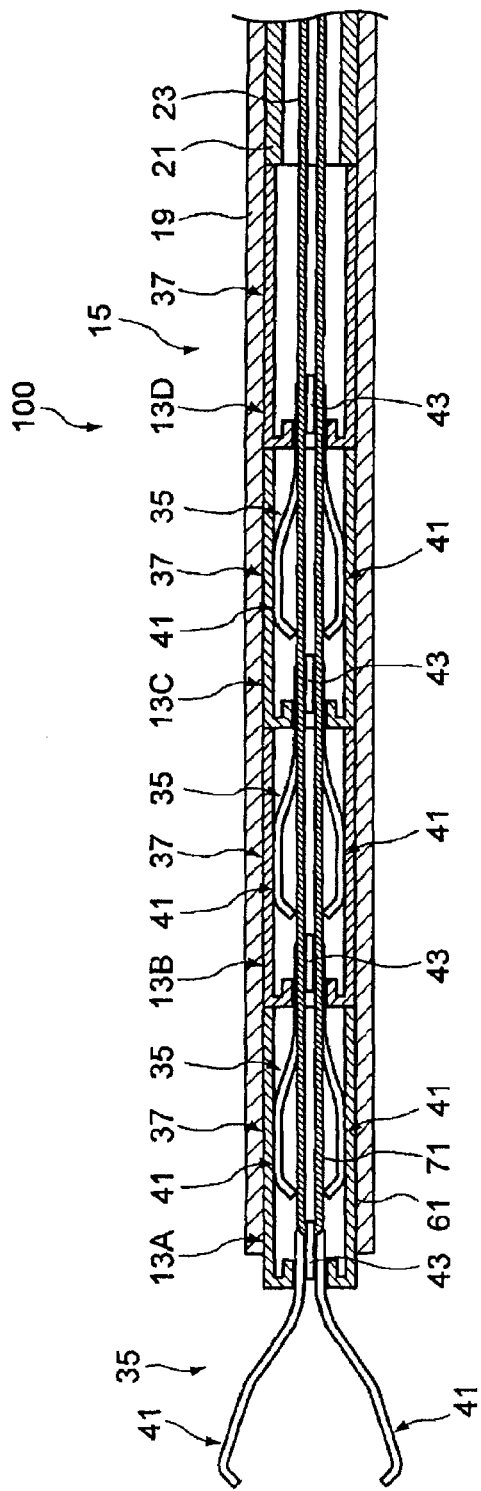
FIGS. 8A and 8B are a vertical cross-sectional view and a horizontal cross-sectional view of the ligation device in which a plurality of clip units are loaded within an outer sheath member.
Figure 8B:
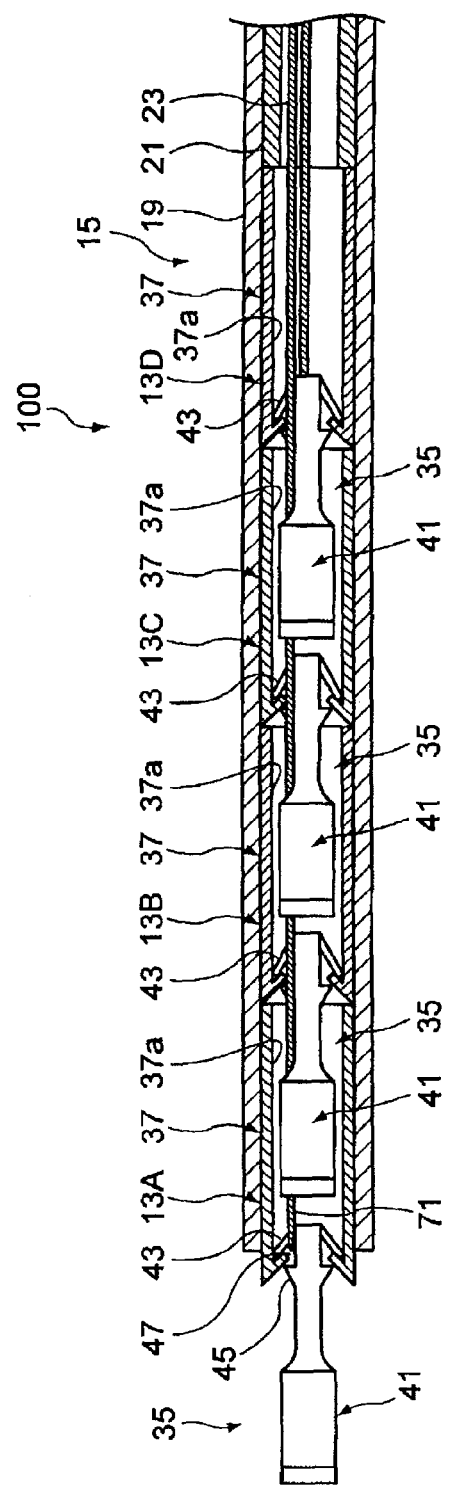
Figure 9:
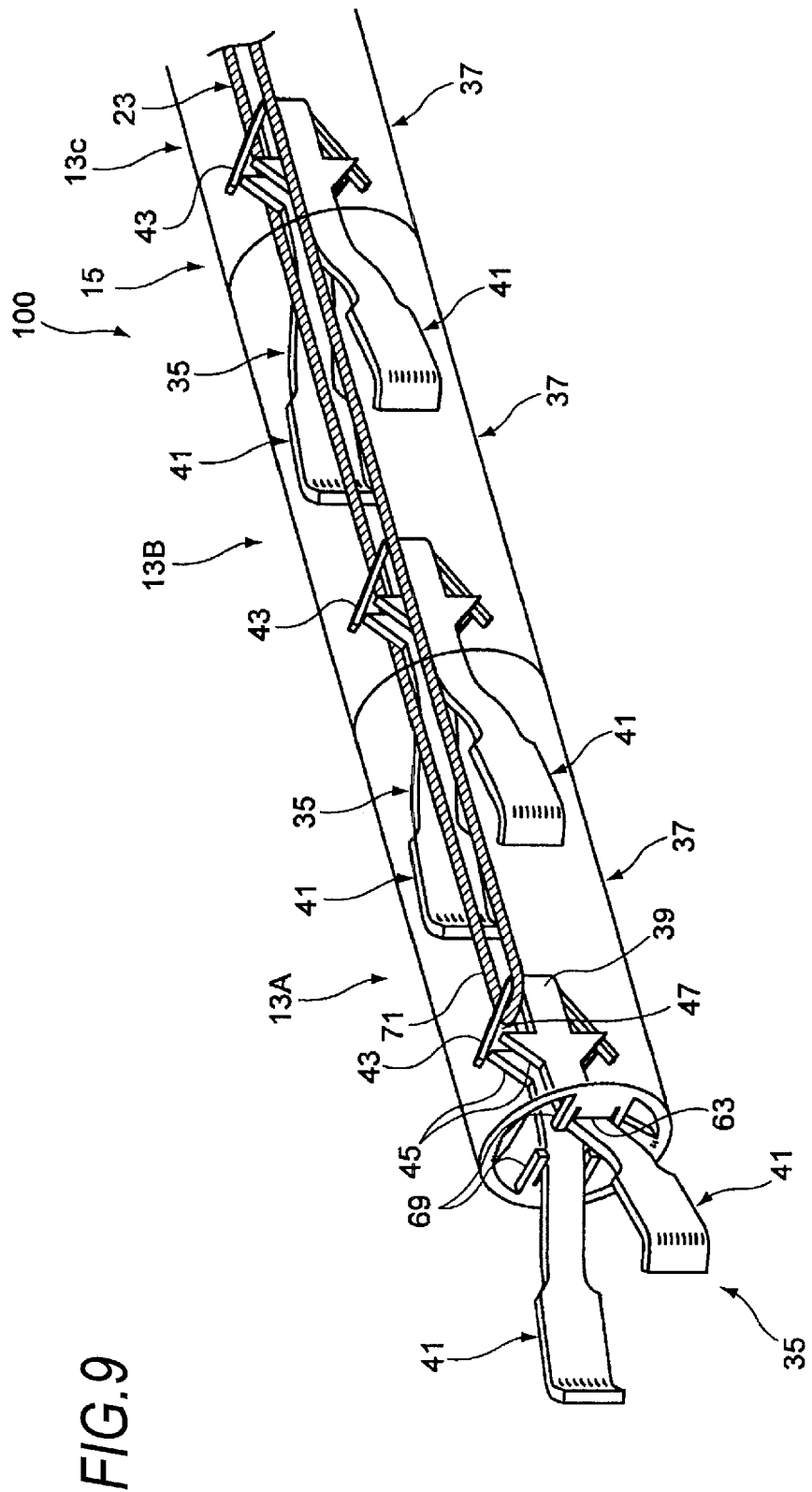
FIG. 9 is a perspective view illustrating the ligation device in FIGS. 8A and 8B in a state where the outer sheath member is removed.

FIG. 8A is a vertical cross-sectional view of the ligation device in which a plurality of clip units are loaded within an outer sheath member, FIG. 8B is a horizontal cross-sectional view thereof, and FIG. 9 is a perspective view of a main part of the ligation device which is illustrated except the outer sheath member. Meanwhile, in the description as below, the same member as in a member illustrated in FIGS. 1 to 7C is referred as the same reference numeral and the description thereof will be omitted.

As illustrated in FIGS. 8A, 8B and 9, the ligation device 100 according to the present configuration is configured such that a plurality of clip units 13 each being constituted by a clip body 35 and a fastening ring 37 are inserted into the outer sheath member 19 in a state where the clip units are arranged in series within the outer sheath member 19. Rotation position of each clip unit 13 is restricted within the outer sheath member 19 by inserting the engagement claws 43 of the clip body 35 into the loop part 71 of the manipulation wire 23. In the illustrated example, whole clip units 13 are loaded within the outer sheath member 19 in the same rotation posture.

The manipulation wire 23 is inserted through each of the plurality of fastening ring 37, and the loop part 71 of the manipulation wire 23 has at least a total length as long as the length of the plurality of clip units 13 which are arranged in a line. The front end of the loop part 71 is inserted through a gap 47 of a clip unit 13A disposed in the distal end of the outer sheath member 19, the gap being defined by engagement claws 43 of a clip body 35, disengagement prevention parts 45 and end surfaces of the base end section 39 in a width direction, as illustrated in FIG. 3. That is, the manipulation wire 23 is engaged with the engagement claws 43 of the leading clip unit 13A. Further, the front end of each engagement claws 43 of rear clip units 13B, 13C, 13D is contacted to the inner peripheral surface 37a of the fastening ring 37 in a state where each engagement claws 43 are inserted into the loop part 71.

A pair of arm parts of each clip body 35 of the clip units 13A, 13B, 13C, 13D which are arranged in a line is configured such that a pair of arm parts 41 of a clip body 35 disposed at the rear side are accommodated within a fastening ring 37 that is nearly disposed at the front side. Therefore, when the insertion part 14 of the ligation device 100 is introduced into a body cavity, each fastening ring 37 receives an external force generated according to the insertion operation to prevent the external force from acting on the clip body 35. Therefore, although the insertion part 15 is curved and introduced into the body cavity in a state where fastening rings 37 are bended to each other, the clip body 35 may be protected by the fastening ring 37 to prevent the clip body 35 from being broken.

Further, since the plurality of clip units 13A, 13B, 13C, 13D are arranged in the same rotation posture, the loop part 71 of the manipulation wire 23 may be engaged with the engagement claws 43 of the rear clip unit 13B after the engagement with the leading clip unit 13A is released. In the same way, as the loop part 71 may be orderly engaged with the engagement claws 43 for the rear clip units 13C, 13D, a repeat ligation performed by bringing up each clip body 35 sequentially may be used.

<Repeating Bring-Up Sequence of Clip Unit>

Here, repeating bring-up sequence of clip units by the above configuration of the ligation device will be described.

FIGS. 10A to 10F are schematic perspective views illustrating the repeated ligation sequence by the ligation device. First, an insertion part 15 is introduced within a body cavity in advance through a channel of an endoscope inserted in the body cavity in advance, the front end of the insertion part 15 is disposed in a portion of a biological tissue to be ligated while monitoring the inside of the body cavity using the endoscope. And then, as illustrated in FIG. 10A, a pair of arm parts 41 of a clip unit 13A disposed in the lead of an outer sheath member (not illustrated) are opened. Meanwhile, since manipulations for open and close of the arm parts 41 are the same as that as described above, the description thereof will be omitted.

Next, as illustrated in FIG. 10B, the manipulation wire 23 is pulled with respect to an inner sheath member, the loop part 71 of the manipulation wire 23 pulls a clip body 35 of a leading clip unit 13A into the fastening ring 37 through the engagement claws 43 of the leading clip unit 13A which is engaged. Therefore, the pair of arm parts 41 of the clip unit 13A are guided by the clip contact parts 63 to be closed, thereby gripping the biological tissue 81 between the tissue gripping units 55, 55.

Figure 11:
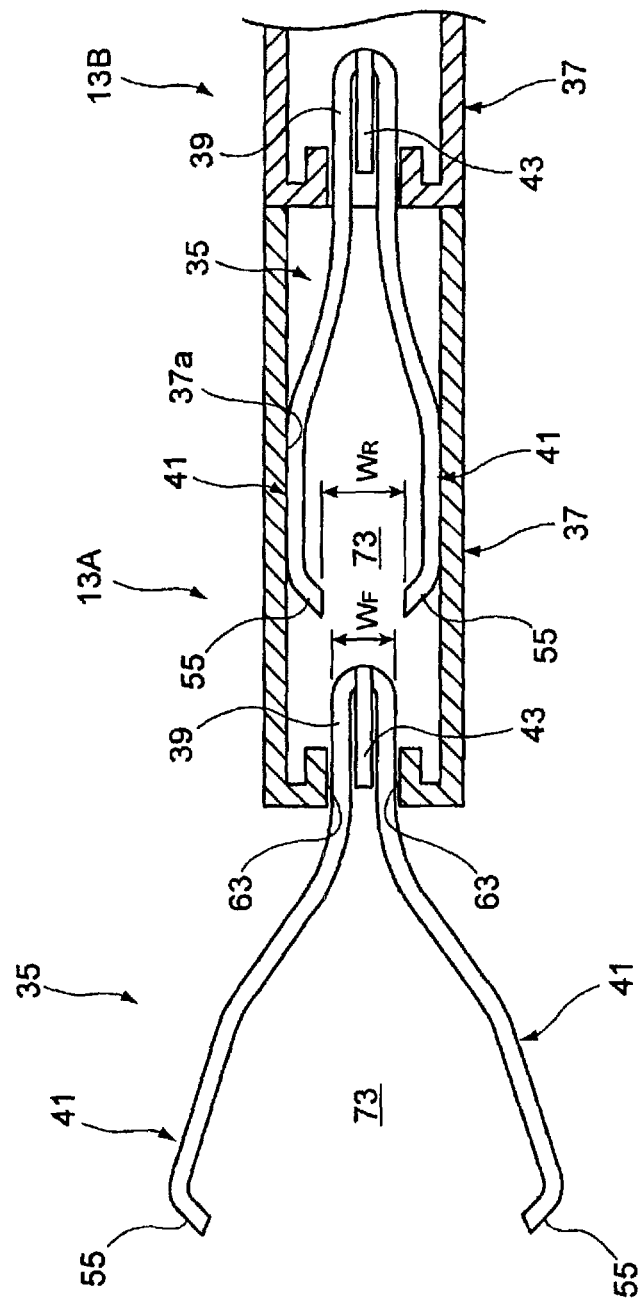
FIG. 11 is a cross-sectional view of a main part illustrating a dimensional relationship between a width of an opening of the arm parts of the clip part inserted into the fastening ring and a width of the base end portion of the clip body.

As illustrated in FIG. 11, the base end section 39 of the clip body 35 of the clip unit 13A is inserted into the arm parts 41 of the clip unit 35 of the rear clip unit 13B. For that reason, the maximum width WF of the base end section 39 in the direction where the arm parts 41 are largely opened with respect to the clip body 35 of the clip unit 13A is set to be smaller than the opening width WR of the pair of arm parts 41 (tissue gripping units 55) of the clip body 35 of the rear clip unit 13B, which is resiliently biased and is in contact with the inner peripheral surface 37a of the fastening ring 37. Accordingly, when the clip body 35 of the clip unit 13A is pulled into the fastening ring 37, the base end section 39 of the clip body 35 of the clip unit 13A is inserted into the arm parts 41 of the clip body 35 of the rear clip unit 13B.

With configuration as described above, the length of the fastening ring 37 in the axis direction may be shorted, and thus, the insertion part 15 in which each clip units 13A, 13B, 13C, 13D are arranged in a line and accommodated therein may be easily bendable to improve the flexibility thereof. Therefore, curve maneuverability when being inserted into the body cavity and shape-following performance for the pipe line within the biological cavity may be improved.

Figure 12:
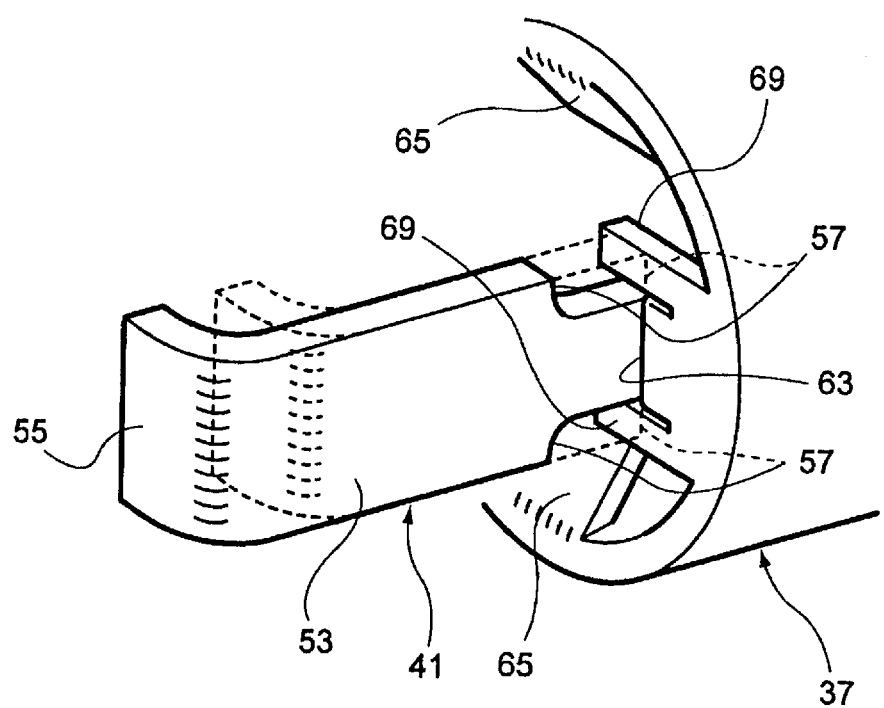
FIG. 12 is an enlarged perspective view of a main part of the clip unit in FIG. 3.

When the manipulation wire 23 is pulled as illustrated in FIG. 10B, the step part 57 between the plate shaped member 51 and the large width portion 53 of each arm part 41 in the clip body 35 of the leading unit 13A, which is illustrated in FIG. 12, is in contact with each of the pair of guide members 69, thereby restricting the movement of the clip body 35 toward the rear side. In this state, when the manipulation wire 23 is further pulled as illustrated in FIG. 10C, the engagement claws 43 of the leading clip body 35 begins plastic deformation in the pull direction of the manipulation wire 23. Therefore, the engagement claws 43 are much plastically deformed to release the engagement between the engagement claws 43 and the loop part 71, as illustrated in FIG. 10D. At this time, the tissue gripping unit 55 of the leading clip body 35 maintains the ligation of the biological tissue 81.

As described above, according to the ligation device 100 of the present configuration, since the separation of the manipulation wire 23 and the clip body 35 is performed by the plastic deformation of the engagement claw 43 regardless of the crack of the member, no cracked piece is generated to surely prevent the obstacle caused by the cracked piece.

Next, when the manipulation wire 23 is pulled as illustrated in FIG. 10E, the loop part 71 disengaged from the leading clip body 35 is guided into the inclined surface 45a of the disengagement prevention part 45 of the clip body 35 adjacently disposed in the rear side, is moved toward the outside of the fastening ring 37 in the diameter direction to contact with the inner surface of the engagement claws 43.

In addition, as illustrated in FIG. 10F, the engagement claws 43 are slightly plastic deformed by the pull of the manipulation wire 23, and thus, the loop part 71 of the manipulation wire 23 enters the gap 47 that is defined by the engagement claws 43, the disengagement prevention part 45 and the width-direction sectional surface of the base end section 39. Accordingly, the manipulation wire 23 and the engagement claws 43 of the clip body 35 of the next clip unit 13B are automatically engaged with each other, and thus, the preparation for the ligation of a next biological tissue is completed. Further, the clip unit 13A is separated from the ligation device 100, and remains in the body cavity in a state where the clip unit 13A ligates the biological tissue.

As described above, according to the ligation device 100 of the present configuration, every time when the ligation of the biological tissue is completed, the insertion part 15 of the ligation device 100 may ligate a plurality of portions of biological tissues sequentially while being inserted in the body cavity without picking-out from the body cavity. For that reason, the effective ligation may be possible to lighten the burden for patients.

Figure 13A:
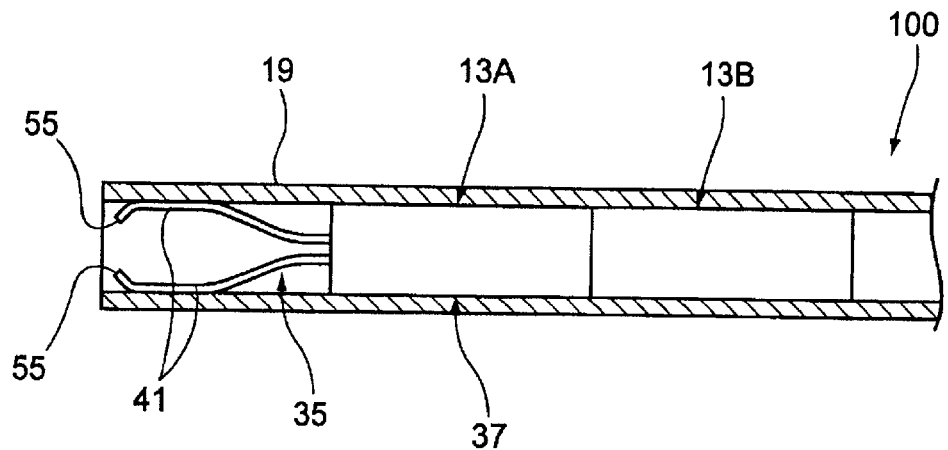
FIG. 13A is a cross-sectional view of the clip body in a state where the clip body is accommodated within the outer sheath member and the arm parts are closed.
Figure 13B:
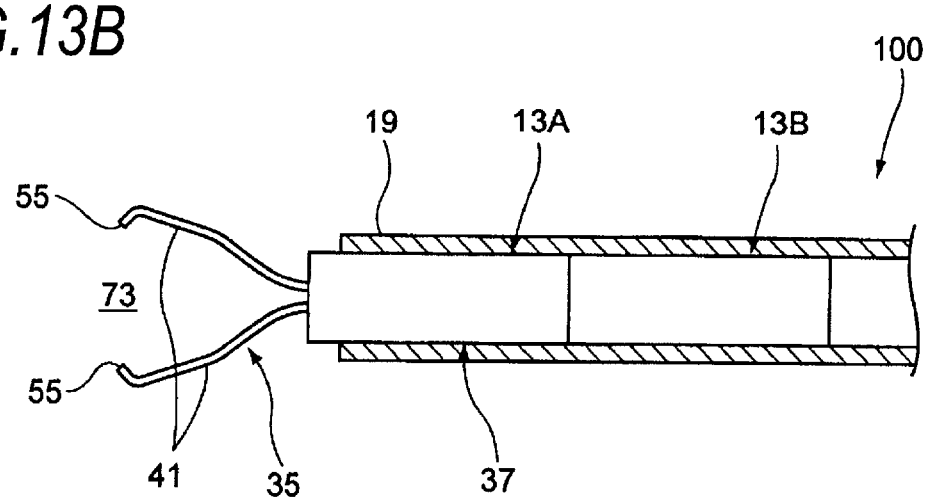
FIG. 13B is a cross-sectional view illustrating a state where the outer sheath member is retracted and the arm parts of the clip body are opened.
Figure 13C:
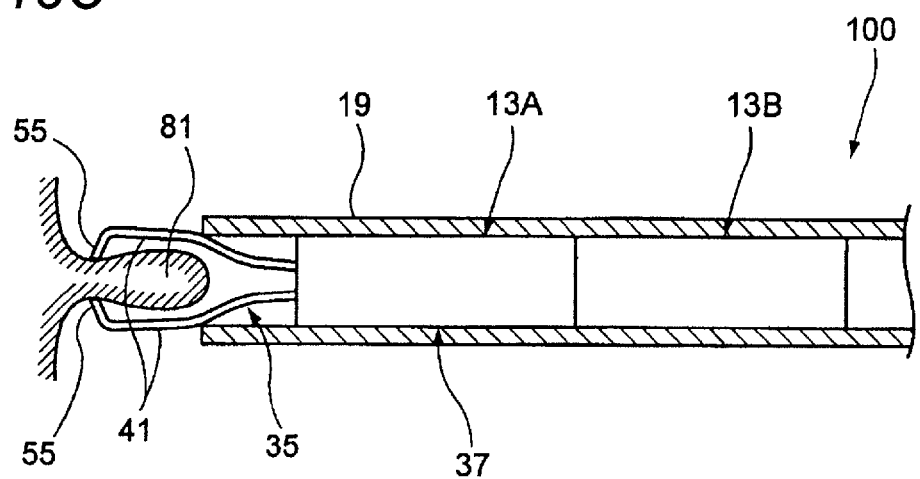
FIG. 13C is a cross-sectional view illustrating a state where the outer sheath member is moved forward and the biological tissue is temporarily fixed by a pair of arm parts.

Meanwhile, although the above-described description describes that the pair of arm parts 41 are opened/closed by the bringing-up and pulling of the manipulation wire 23, the pair of arm parts 41 may be opened/closed by reciprocating the outer sheath member 10 with respect to the inner sheath member 21, as illustrated in FIGS. 13A to 13C. Specifically, a pair of arm parts 41 closed and accommodated within an outer sheath member 19 in a closed state, as illustrated in FIG. 13A. When the outer sheath member 19 is retreated, the restriction for the arm parts 41 by the outer sheath member 19 is released and the arm parts 41 are opened, thereby forming a narrowed gap 73 between the pair of arm parts 41, as illustrated in FIG. 13B.

Next, as illustrated in FIG. 13C, when the narrowed gap 73 is disposed against a biological tissue and the outer sheath member 19 is advanced, the outer surface of the pair of arm parts 41 are in contact with the inner peripheral surface of the outer sheath member 19 to be closed. Therefore, the pair of arm parts 41 grasp the biological tissue 81. As described above, by reciprocating the outer sheath member 19, a pair of arm parts 41 may be opened/closed to temporarily fix the biological tissue 81. Then, after confirming that the biological tissue 81 to be processed is grasped by the pair of arm parts 41, the manipulation wire 23 is pulled to ligate the biological tissue 81 as described in FIGS. 10A to 10F.

<Connecting Unit for Adjacent Clip Units>

Figure 14:
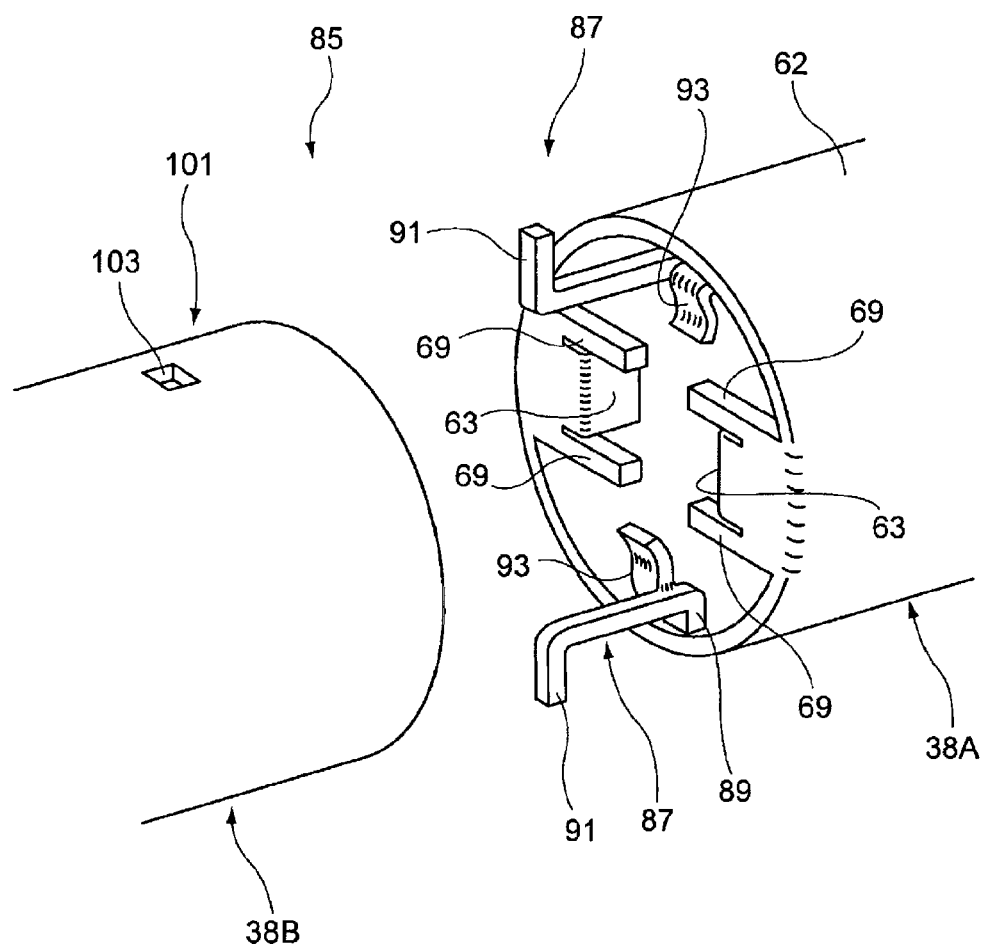
FIG. 14 is a perspective view of a connecting mechanism of a clip unit.
Figure 15:
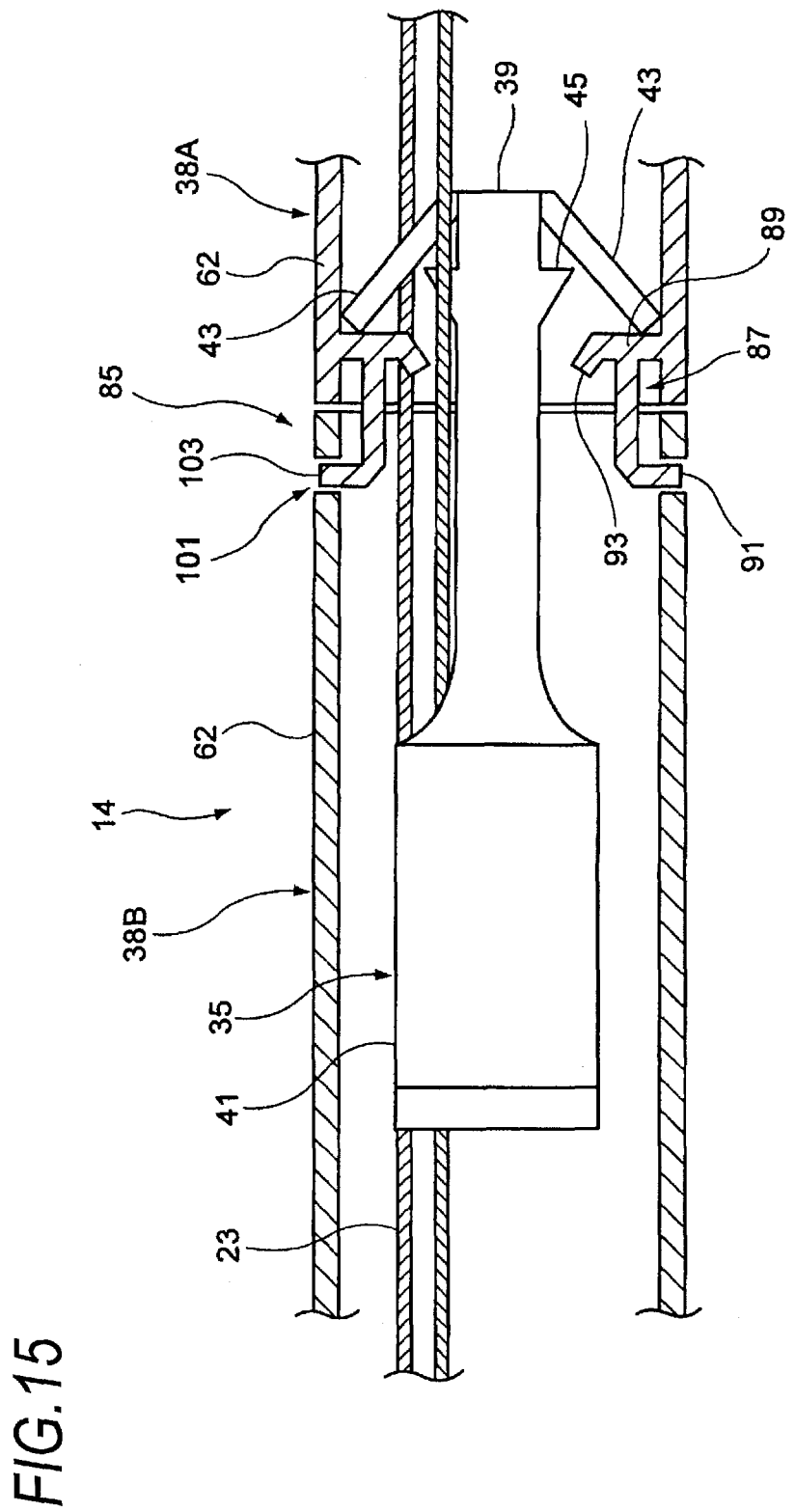
FIG. 15 is a cross-sectional view of a main part of the connecting mechanism of the clip unit in FIG. 14.

Next, the connecting mechanism (connecting unit) for the adjacent clip units will be described. FIG. 14 is a perspective view of an configuration example of a connecting mechanism of a clip unit, FIG. 15 is a cross-sectional view of a main part of the connecting mechanism of the clip unit in FIG. 14, and FIGS. 16A to 16D are cross-sectional views illustrating states where the engagement of the connecting mechanism in FIG. 15 is released step by step.

In the fastening ring of the present configuration, fastening rings 38A, 38B which are adjacent in the front-rear direction are connected with each other by a connecting mechanism 85. The connecting mechanism 85 includes a locking member 87 configured to be formed extendedly from a fastening ring 38A at one side to a fastening ring 38B at the other side, and a fitting support 101 formed at the fastening ring 38B at the other side to be fitted with the locking member 87. In addition, each of the fastening rings 38A, 38B is assembled with clip body 35 to form a clip unit 14.

The locking member 87 includes: a base part 89 provided in the front end side of the fastening ring 38 and protruded toward the inner side in the diameter direction from the inner peripheral surface of a cylindrical part 62; a support shaft 91 (first fitting part) configured to be branched from the base part 89 to extended to the forward in the axis direction, and bent to the outer side in the diameter direction; and a wire engagement member 93 configured to be branched from the base part 89 to be extended to the inner side in the diameter direction. The wire engagement member 93 of which a portion from a middle part on the extended to the front end is bent toward the forward in the axis direction. The fitting support 101 is provided at the rear end side of the fastening ring 38, and includes a fitting hole 103 (second fitting part) to be capable of fitting with the support shaft 91 (first fitting part).

The support shaft 91 (first fitting part) of the locking member 87 is resiliently fitted with the fitting hole 103 (second fitting part) of the fitting support 101, thereby connecting the fastening rings 38A, 38B each other. Meanwhile, the contacting surfaces of the end surfaces of the fastening rings 38A, 38B may be formed in a circular arc shape when viewed from a direction perpendicular to the axis direction (see FIG. 26), the support shaft 91 of the connecting mechanism 85 may be disposed in the center of curvature of the circular arc shape of the contacting surfaces. Therefore, even though the fastening rings 38A, 38B are bent, the fitting between the support shaft 91 (first fitting part) and the fitting hole 103 (second fitting part) may be smoothly operated without releasing, thereby maintaining the connection of the both fastening rings 38A, 38B stably.

Next, the release of the fitting of the connecting mechanism 85 will be described with reference to FIGS. 16A to 16D.

Figure 16A:
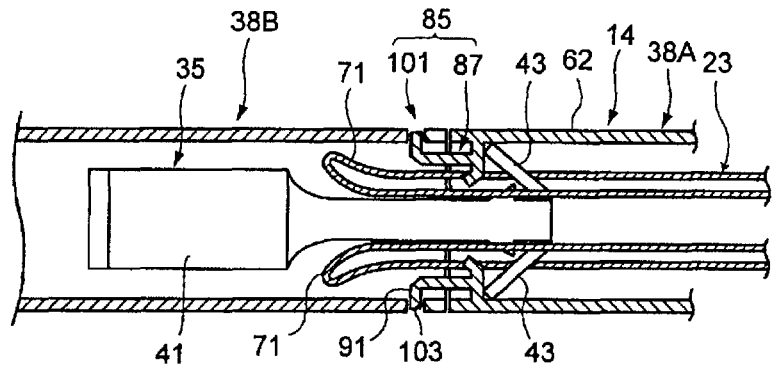
FIGS. 16A to 16D are cross-sectional views illustrating states where the fitting of the connecting mechanism in FIG. 15 is released step by step, respectively.
Figure 16B:
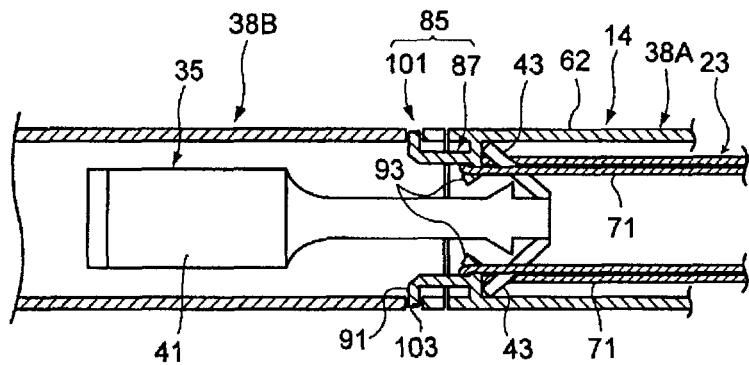
Figure 16C:
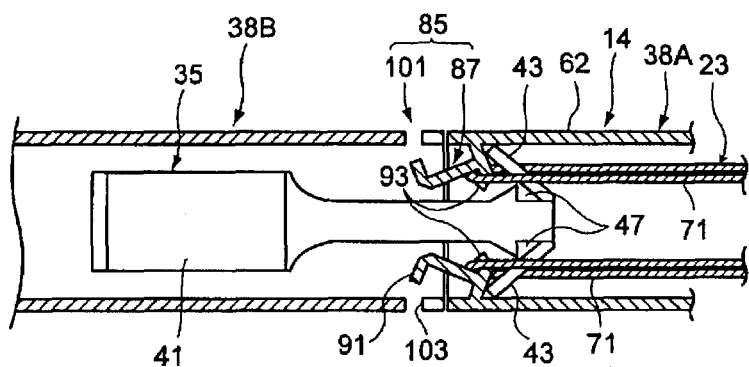

FIGS. 16A to 16D are cross-sectional views illustrating states where the fitting of the connecting mechanism is released step by step, respectively. FIG. 16A illustrates a state where the fitting between the loop part 71 of the manipulation wire 23 and the clip body 35 at the front side (not illustrated) is released, which corresponds to FIG. 10D. When the manipulation wire 23 of which fitting with the clip body 35 is released is pulled, the loop part 71 of the manipulation wire 23 is engaged with the wire engagement member 93 protruded toward the inner side of the fastening ring 38 from the base part 89 of the locking member 87, as illustrated in FIG. 16B. Furthermore, as illustrated in FIG. 16C, when the manipulation wire 23 is pulled, the wire engagement member 93 is resiliently or plastically deformed by the pulling force, thereby drawing out the support shaft 91 (first fitting part) from the fitting hole 103 (second fitting part). Accordingly, the fitting of the connection mechanism is released to separate the fastening rings 38A, 38B.

Figure 16D:
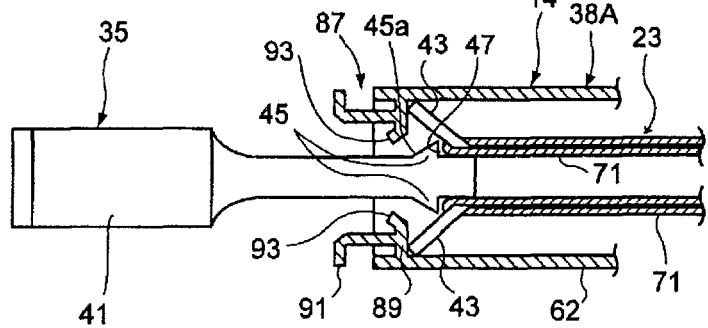

In addition, as illustrated in FIG. 16D, the loop part 71 disengaged from the leading clip body 35 is guided into the inclined surface 45a of the disengagement prevention part 45 of the clip body 35 disposed in the rear side, is moved toward the outside of the fastening ring 38A in the diameter direction. Then, the loop part 71 is in contact with the inner surface of the engagement claws 43 to be entered into the gap by plastically deforming the engagement claws 43 slightly. Accordingly, the manipulation wire 23 and the engagement claws 43 of the clip body 35 of the next clip unit 14 are automatically engaged with each other, and thus, the preparation for the ligation of a next biological tissue is completed.

Meanwhile, in the illustrated exemplary embodiment, a configuration where two sets of a locking member 87 and a fitting hole 103 are formed at different positions in the peripheral direction is depicted, but a configuration where only a fitting of any one set is released may be used. At that case, the fitting of the one set is released, the fastening ring is displaced, and then the fitting of the other set is automatically released. Further, as illustrated in FIGS. 16A to 16D, when a loop part 71 of a manipulation wire 23 is engaged with each of the both set and the both set are disengaged at the same time, the releasing operation of the connection may be surely performed.

<Modified Example of Connecting Mechanism>

Figure 17:
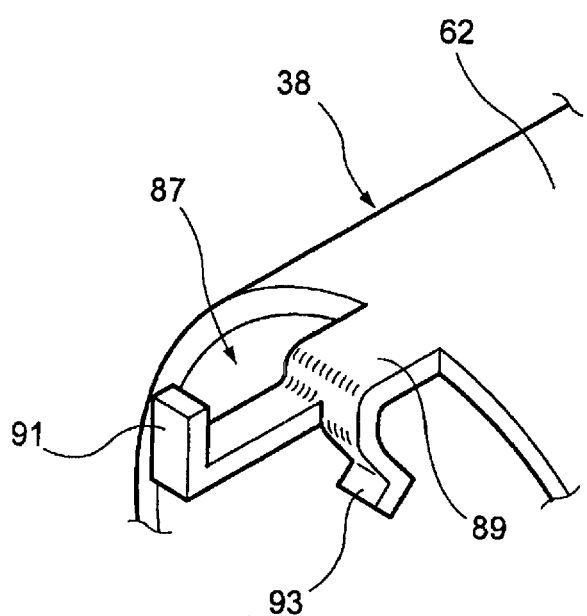
FIG. 17 is an enlarged perspective view of a main part of a modified example of a connecting mechanism.
Figure 18A:
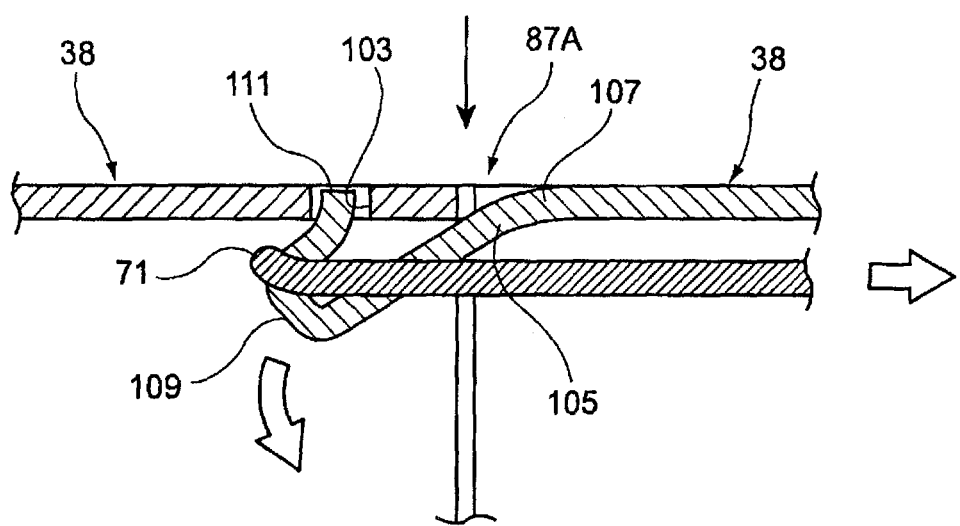
FIG. 18A is a cross-sectional view of a main part of a connecting mechanism of a clip unit according to another modified example.
Figure 18B:
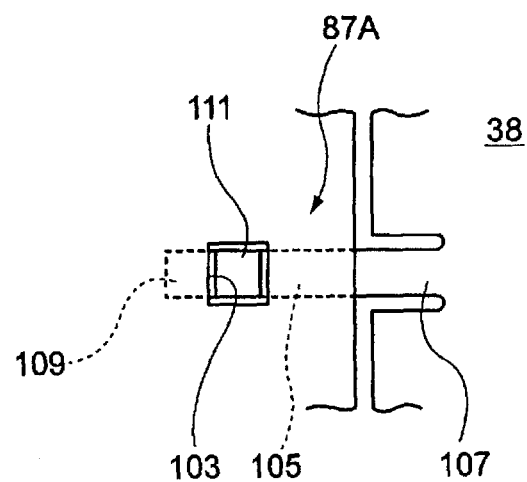
FIG. 18B is a view shown in the Z-direction indicated by an arrow in FIG. 18A.

FIG. 17 is an enlarged perspective view of a main part of a modified example of the connecting mechanism. As illustrated in FIG. 17, a locking member 87 of a connecting mechanism 85 of the modified example is configured such that a base part 89 is extended toward the front side from the front end of a fastening ring 38 (cylindrical part 62) and bent to the inner side in the diameter direction. Since other configuration and action thereof are the same as in the connecting mechanism 85 described in FIGS. 14 to 16D, the same reference numeral is attached to the same part and the description thereof will be omitted.

Further, the locking member of the connecting mechanism may be a locking member 87A configured such that a band shaped-plate part 105 protruded to the front side from the fastening ring 38 (cylindrical part 62) is bent. The locking member 87A includes: a band shaped-plate part 105 bent toward the inner side of the fastening ring 38 from an origin part 107 branched from the fastening ring 38 and extended to be inclined to the inner side in the diameter direction toward the forward side (a direction toward other fastening ring 38); a wire engagement part 109 formed curvedly in a substantial U shape toward the outer side in the diameter direction from the band shaped-plate part 105; and a support shaft 111 (first fitting part) provided at the front end of the wire engagement part 109 and protruded to the outer side in the diameter direction.

The support shaft 111 (first fitting part) of the locking member 87A in the configuration example is fitted with the fitting hole 103 (second fitting part) of the fastening ring adjacent in the forward side by the resilient force thereof, thereby connecting the fastening rings 38 each other. In addition, the connection of the fastening rings 38 each other is released by engaging the loop part 71 of the manipulation wire 23 with the wire engagement part 109, pulling the manipulation wire 23 to deform the locking member 87A resiliently, and drawing out the support shaft 111 (first fitting part) from the fitting hole 103 (second fitting part), thereby separating the fastening rings 38 from each other.

<Other Configuration Example of Connecting Unit>

Figure 19:
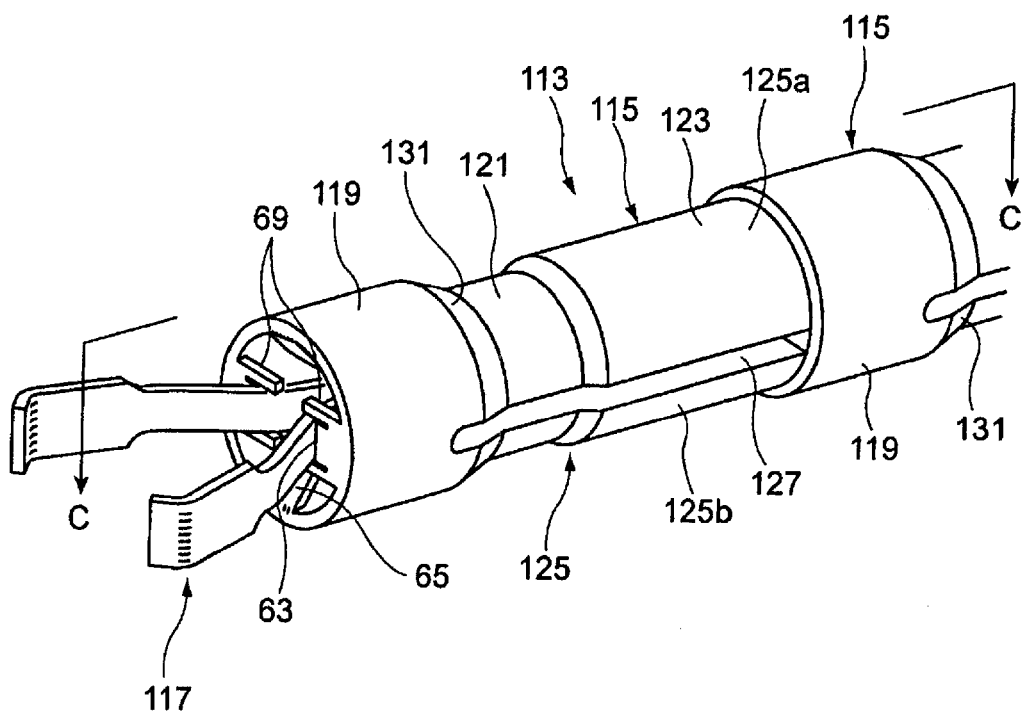
FIG. 19 is a perspective view of a connecting mechanism according to another configuration example.

Next, other configuration example of the connecting mechanism (connecting unit) will be described with reference to FIGS. 19 to 23B. FIG. 19 is a perspective view of the other connecting mechanism, FIG. 20 is a cross-sectional view of a main part of the connecting mechanism, and FIG. 23A is a side view of an appearance of FIG. 20.

Figure 20:
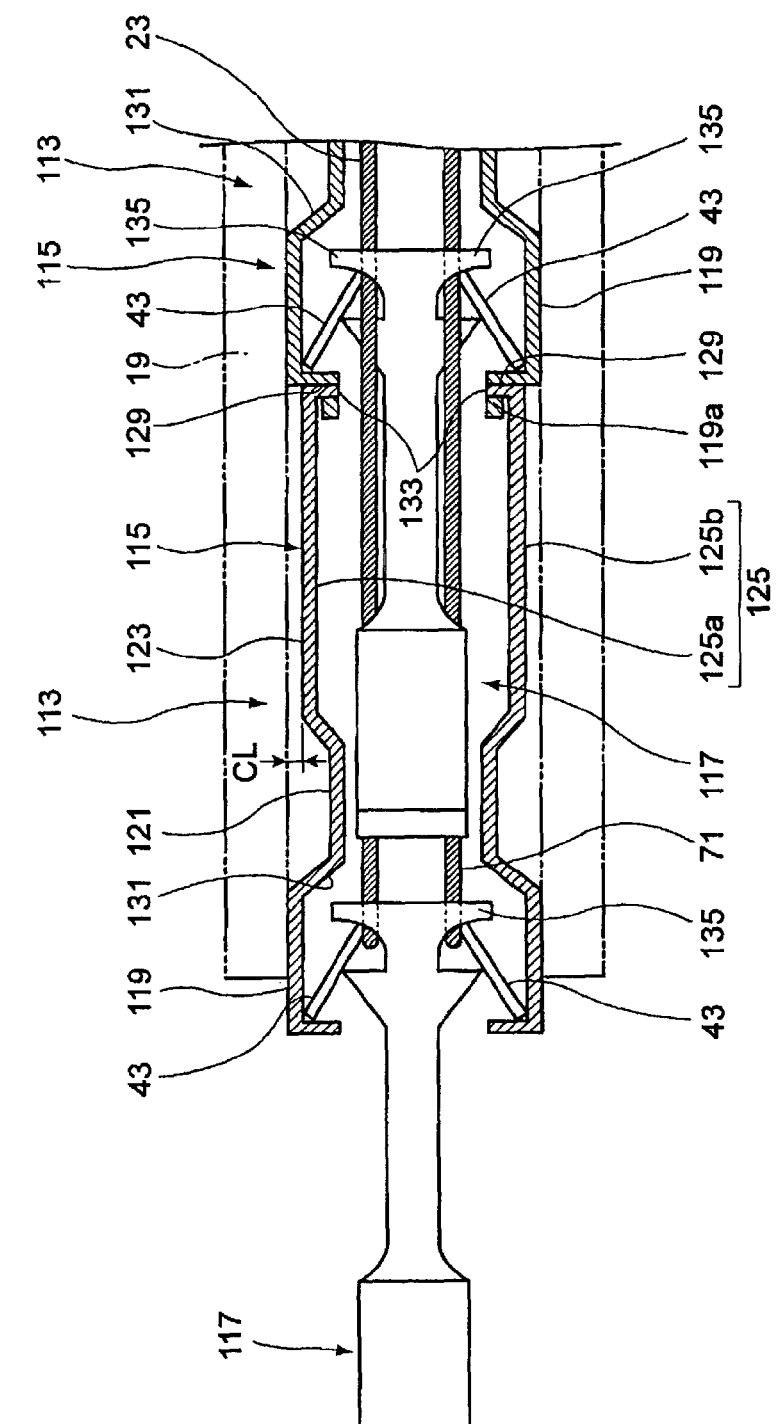
FIG. 20 is a cross-sectional view taken along line C-C in FIG. 19.

As illustrated in FIGS. 19, 20 and 23A, a clip unit 113 of the present configuration example is constituted by a fastening ring 115 and a clip body 117 to be inserted into the fastening ring 115, and is disposed in series along the axis direction from a distal end of an outer sheath member 19. The fastening ring 115 includes a large diameter part 119 formed in the front end side and having an outer diameter slightly smaller than the inner diameter of the outer sheath member 19, a diameter reducing part 121 formed continuously from the large diameter part 119 and having a small diameter, and a middle diameter part 123 formed continuously from the diameter reducing part 121 and having an outer diameter which is the middle between the large diameter part 119 and the diameter reducing part 121.

Therefore, when the clip unit 113 is inserted into the outer sheath member 19, a diameter direction gap CL is formed between the middle diameter part 123 and the inner diameter of the outer sheath member 19. The diameter direction gap CL is used to release the connection, which will be described later. The large diameter part 119, the diameter reducing part 121 and the middle diameter part 123 form a cylindrical part 125.

The cylindrical part 125 is provided with a pair of diameter enlarging slits 127 cut-off along the axis direction up to a position beyond the diameter reducing part 121 from the end of the middle diameter part 123, which is an end opposite to the insertion side of the clip body 117 of the fastening ring 115. The respective diameter enlarging slits 127 are formed in different circumference positions by 180 degrees to each other, and the cylindrical part 125 includes semi-cylindrical parts 125a, 125b divided into two in the diameter direction by the diameter enlarging slits 127. The semi-cylindrical parts 125a, 125b form a cylindrical shape in normal state, and when an external force is applied to the clip body 117 as described below, the rear ends (ends opposite to the insertion side of the clip body) of the semi-cylindrical parts 125a, 125b are resiliently deformed in a direction where they are spaced from each other toward the outer side in the radial direction.

The front end of the large diameter part 119 is provided with a connecting part 119a having a diameter that is capable of being inserted into the middle diameter part 123, that is, slightly smaller than the inner diameter of the middle diameter part 123. The connecting part 119a is provided with a pair of fitting holes 129 (second fitting part) formed in the different circumference positions by 180 degrees. The fitting holes are formed such that they penetrate the connecting part 119a in the diameter direction. In addition, the large diameter part 119 is provided with a clip contacting part 63, a clip disengagement prevent member 65 and a guide member 69, which are already described with reference to FIG. 2. Therefore, the description thereof will be omitted.

The diameter reducing part 121 has an conical shaped-inclined surface 131 of which diameter is reduced toward the rear side from the large diameter part 119, and is connected with the large diameter part 119 through the inclined surface 131. The rear end part of the middle diameter part 123 is provided with a pair of support shafts 133 (first fitting part) protruded to the inner side in the diameter direction and in the center in the circumference direction of the two diameter enlarging slits 127. That is, the pair of support shafts 133 (first fitting part) are formed in a place which correspond to the pair of fitting holes 129 (second fitting part), respectively. The support shafts 133 (first fitting part) and the fitting holes 129 (second fitting part) form a connecting unit, and the support shafts 133 are fitted with the fitting holes 129 by the resilient force of the cylindrical part 125, thereby connecting the fastening rings 115 to each other.

Figure 21A:
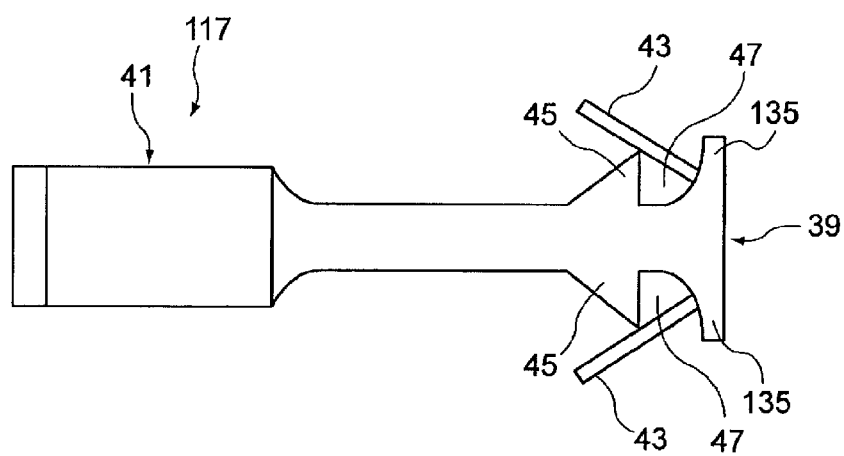
FIGS. 21A and 21B are a side view and a plan view of the clip body illustrated in FIG. 19, respectively.
Figure 21B:
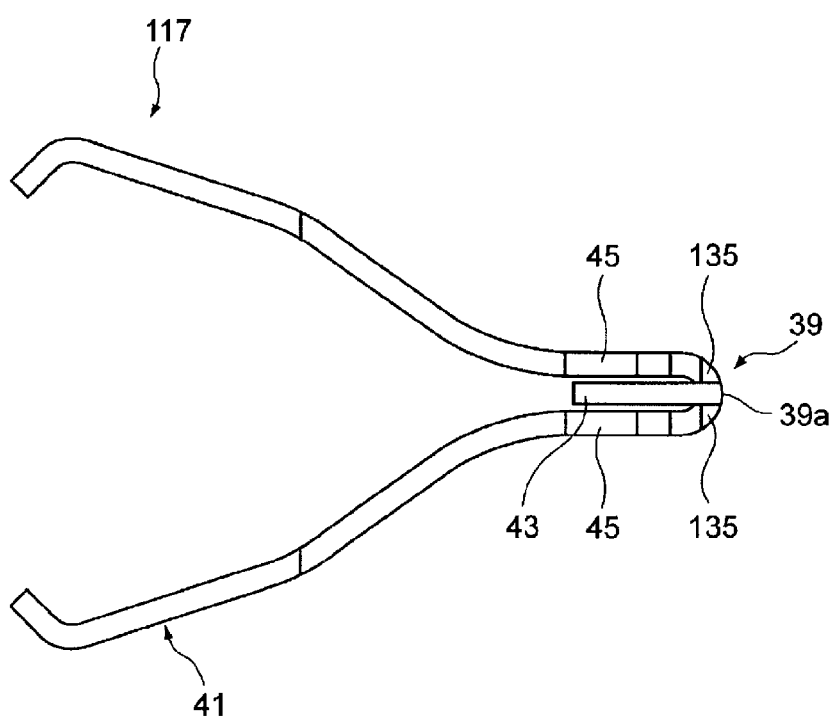

As illustrated in the side view of FIG. 21A, and the plan view of FIG. 21B, the clip body 117 has a shape as in the clip body 35 illustrated in FIGS. 4A and 4B, and includes a base end section 39, a pair of arm parts 41, engagement claws 43, and disengagement prevention parts 45. The clip body 117 is provided with a gap to engage with a loop part 71 of a manipulation wire 23. Further, the base end section 39 of the clip body 117 is provided with protrusions 135 as a disengagement unit. The protrusions 135 are disposed at the rear side of the disengagement prevention parts 45 (bottom part 39a side of the base end section 39) and protruded in a direction perpendicular to the longitudinal direction of the clip body 117 at the both sides of the base end section 39 in the width direction to be formed at the both side of the engagement claws 43 in order to grasps the engagement claw 43. Other configuration and action are the same as the clip body 35 illustrated FIGS. 4A and 4B.

As illustrated in FIG. 20, the plurality of clip units 113, each configured by inserting the clip body 117 including the protrusion 135 as a disconnection unit into the fastening ring 115, are connected by fitting of the support shaft 133 of the fastening ring 115 (first fitting part) and the fitting hole 129 (second fitting part), thereby being inserted to be arranged in a line into the outer sheath member 19 while restricting the rotation positions of the fastening rings 115. The engagement claws 43 of each clip unit 113 is inserted into the loop part 71 of the manipulation wire 23, which is inserted through corresponding fastening ring 115. The front end of the loop part 71 is inserted between a pair of protrusions 135 of the clip unit 113 disposed at distal end of the outer sheath member 19 to be engaged with the engagement claws 43.

Figure 22:
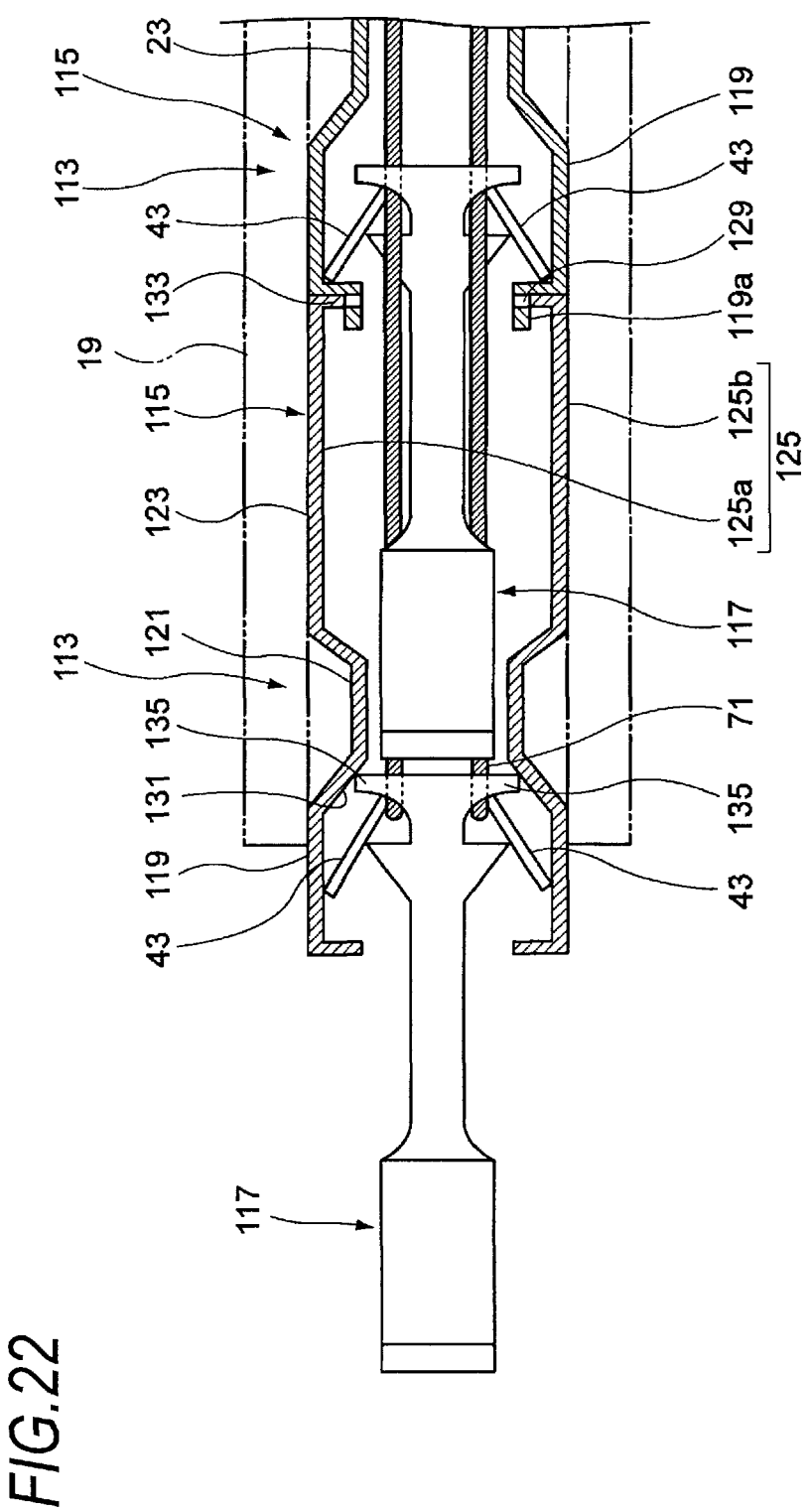
FIG. 22 is a cross-sectional view taken along line C-C in FIG. 19, which illustrates a state where the fitting of the connecting mechanism is released.

FIG. 22 is a cross-sectional view illustrating a state where the fitting of the connecting mechanism is released, and FIG. 23B is a side view of the appearance thereof. When the manipulation 23 is pulled with respect to the inner sheath member 21 and the clip body 117 of the leading clip unit 113 is pulled into the fastening ring 115 using the engagement claws 43, the pair of protrusions 135 become in contact with the inclined surface 131 of the diameter reducing part 121 to press the inclined surface 131 toward the outer side in the diameter direction. Accordingly, the semi-cylindrical parts 125a, 125b are resiliently deformed in a direction where the rear end part opposite to the clip body insertion side are spaced from each other to the outer side in the radial direction, the support shaft 133 (first fitting part) having been fitted with the fitting hole 129 (second fitting part) is disengaged from the fitting hole 129, thereby releasing the connection of the fastening rings 115 each other. At that time, since a diametric gap CL is formed over the entire circumference between the middle diameter part 123 (semi-cylindrical parts 125a, 125b) and the inner diameter of the outer sheath member 19, the connection of the fitting hole 129 and the support shaft 133 is easily released without impeding the resilient deformation of the semi-cylindrical parts 125a, 125b toward the outer side in the diameter direction.

Next, the engagement claws 43 are plastically deformed by the pulling of the manipulation wire 23, and thus, the fitting of the loop part 71 of the manipulation wire 23 and the leading clip body 117 is released to separate the leading clip unit 113. Further, when the manipulation wire 23 is pulled, the loop part 71 is automatically fitted with the engagement claws 43 of the next clip unit 113, and the preparation of the ligation for the next biological tissue is completed.

<Connecting Structure for Adjacent Clip Units>

Figure 24:
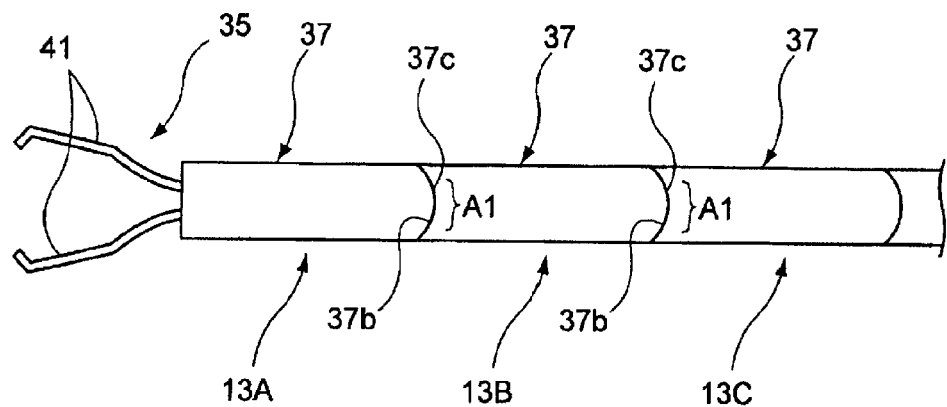
FIG. 24 is a plan view illustrating a plurality of clip units disposed in series in a state where an outer sheath member is removed, as a view for describing another configuration example.
Figure 25:
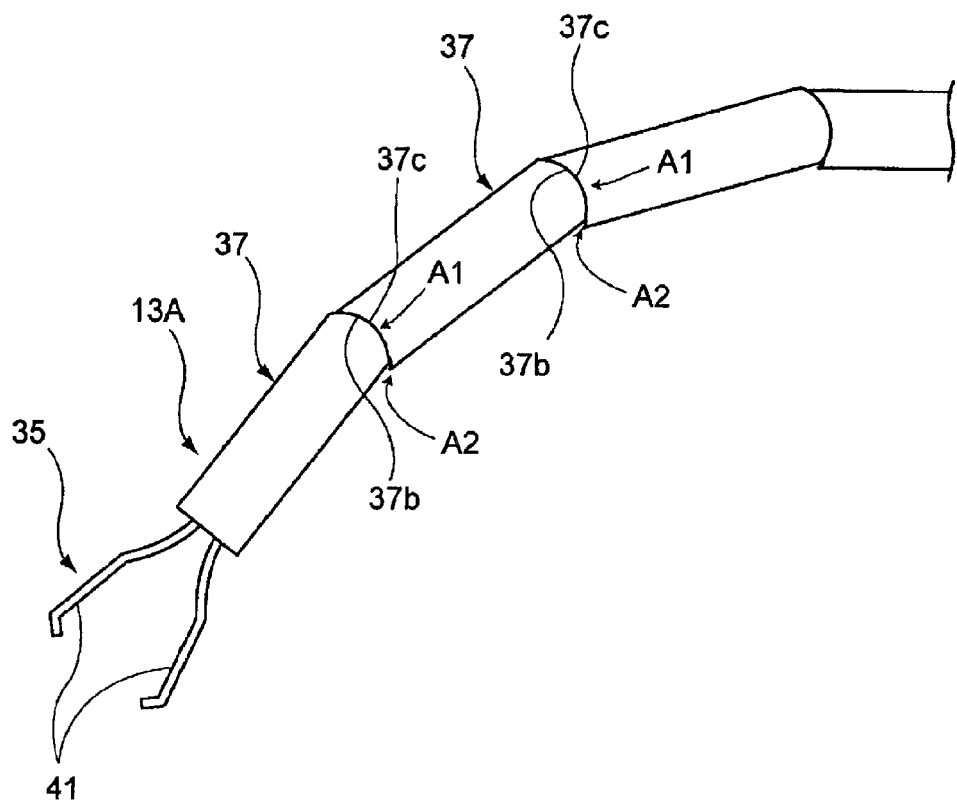
FIG. 25 is a plan view illustrating a state where the ligation device in FIG. 24 is bent.

FIG. 24 is a plan view illustrating a state where a plurality of clip units are arranged in a straight type, and FIG. 25 is a plan view illustrating where a plurality of clip units are bent each other to be arranged in a curved shape. In the configuration of the clip units of the present configuration example, the contact surfaces 37b, 37c of the end surfaces of the adjacent fastening rings 37 each other are formed in a circular arc when viewed from a direction perpendicular to the axis direction of the fastening rings 37 (when viewed from a direction perpendicular to the page of FIG. 24), respectively. By forming the contact surfaces 37b, 37c of the end surfaces of the fastening rings 37 each other in the circular arc when viewed form a direction perpendicular to the axis direction, the fastening rings 37 may be arranged in a inclined state from the axis direction thereof. That is, according to the contact surfaces 37b, 37c formed in the circular arc shape, the adjacent fastening rings 37 each other may be connected to be freely bendable within a plane parallel to the axis direction thereof.

The contact surfaces 37b, 37c of the fastening rings 37 include a contact area A1 that always contact with each other at circumference positions different by at least 180 degrees, regardless of the curve of the fastening rings 37. Further, each of the fastening rings 37 includes a contact-separation area A2 that is in contact in a state where the fastening rings 37 are arranged in the straight type and is not contacted when the fastening rings 37 are bent.

At least, the contact surfaces 37b, 37c at the contact area A1 as described above are formed in a circular arc when viewed from the direction perpendicular to the axis direction of the fastening ring, the curvatures of the circular arcs being the same. Meanwhile, although in the contact area A1 of the clip unit in the illustrated example, the contact surface 37b at the front side in the axis direction is a concave surface and the contact surface 37c at the rear side in the axis direction is a convex surface, but the contact surfaces 37b, 37c may be formed reversely.

Further, in the contact surfaces 37b, 37c of the fastening ring 37, a relief part may be formed which is formed by cutting off the end of the fastening ring 37 in advance at the side to be concave surface of the contact-separation area A2. The relief part may surely prevent the interference of the fastening rings 37 each other without contacting the corresponding contact surface 37b when the adjacent fastening rings 37 are curvedly connected with each other.

Therefore, for the fastening rings 37, the convex surface of the contact surface 37c and the concave surface of the contact surface 37b in the contact area A1 are always be contacted to each other, the fastening rings 37 may be freely bent in the plane parallel to the axis direction of the fastening rings 37. Further, the fastening rings 37 may have flexibility while securing the compression stiffness thereof by the contact area A1 to be always contacted. Therefore, curve maneuverability when being inserted into the body cavity and shape-following performance for the pipe line within the body cavity are improved, thereby lightening the burden for patients. Meanwhile, the contact surfaces 37b, 37c of each fastening ring 37 may be formed in a spherical surface shape in addition to the circular arc when viewed from a direction perpendicular to the axial direction. In this case, the adjacent fastening rings 37 each other may be bent in a random direction.

Figure 26:
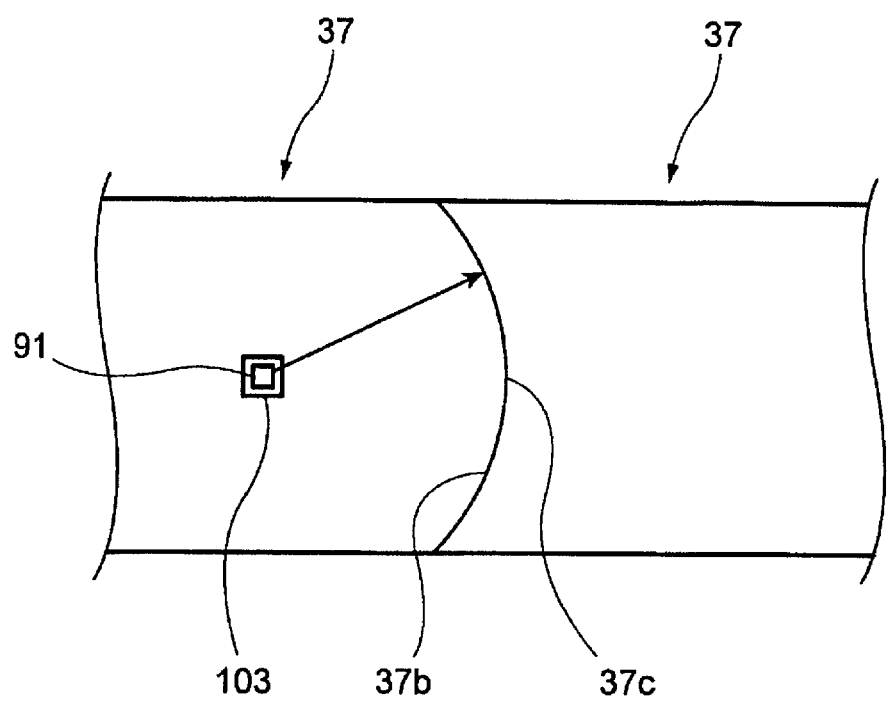
FIG. 26 is a plan view illustrating a relationship between a support shaft and a shape of the end surface of a fastening ring of a connecting mechanism.

As illustrated in FIG. 26, when the adjacent fastening rings 37 are connected with each other by the connecting mechanism, the support shaft 91 of the connecting mechanism is disposed in the center of curvature of the circular arc shape of the contact surfaces 37b, 37c. Therefore, even when the fastening rings 37 are bent, the connecting mechanism may be smoothly operated without releasing the fitting of the connecting mechanism to maintain the connection state of the both fastening rings 37 stably.

The connection configuration of the clip units may be freely bent in two different directions in addition to a single direction as described above.

Figure 27:
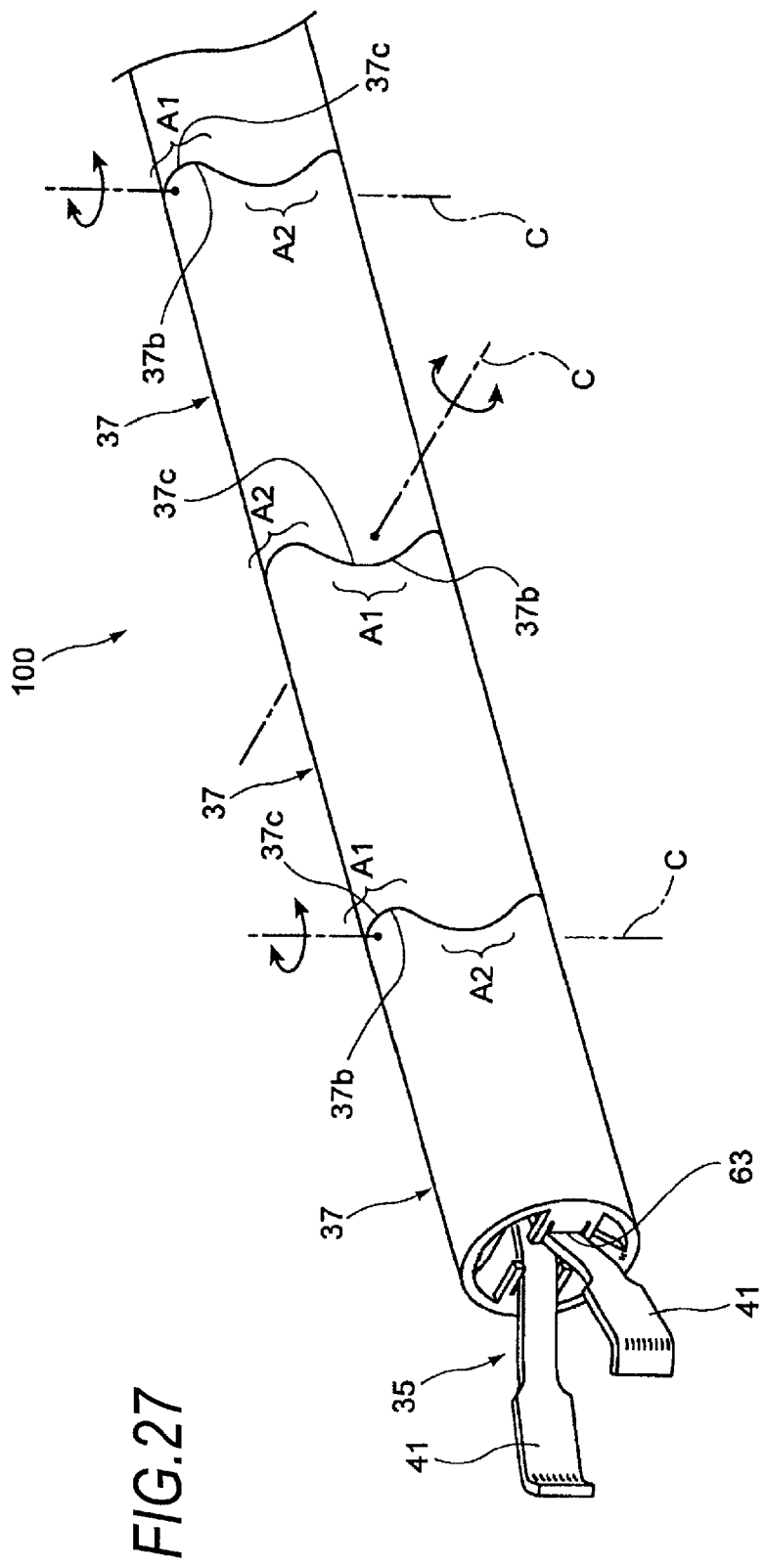
FIG. 27 is a perspective view of clip units disposed in a state where the bending directions of the fastening rings are different alternately by 90 degrees.

FIG. 27 is a perspective view of clip units arranged in a state where the bending directions of the fastening rings are different alternately by 90 degrees. The clip units in the present configuration example are configured such that the bending center axes C of the adjacent fastening rings 37 are different alternately by 90 degrees along the arrangement direction of the clip units. That is, the contact areas A of the contact surfaces 37b, 37c of the end surfaces of the adjacent fastening rings 37 each other are different alternately by 90 degrees.

Therefore, the connected clip units are configured such that the adjacent fastening rings 37 are capable of being bent in two directions to be perpendicular to each other, and as a result, the flexibility of the clip unit is further improved. Accordingly, the curve maneuverability when being inserted into the body cavity and the shape-following performance for the pipe line within the body cavity are further improved.

<Other Configuration Example of Clip Unit>

Figure 28:
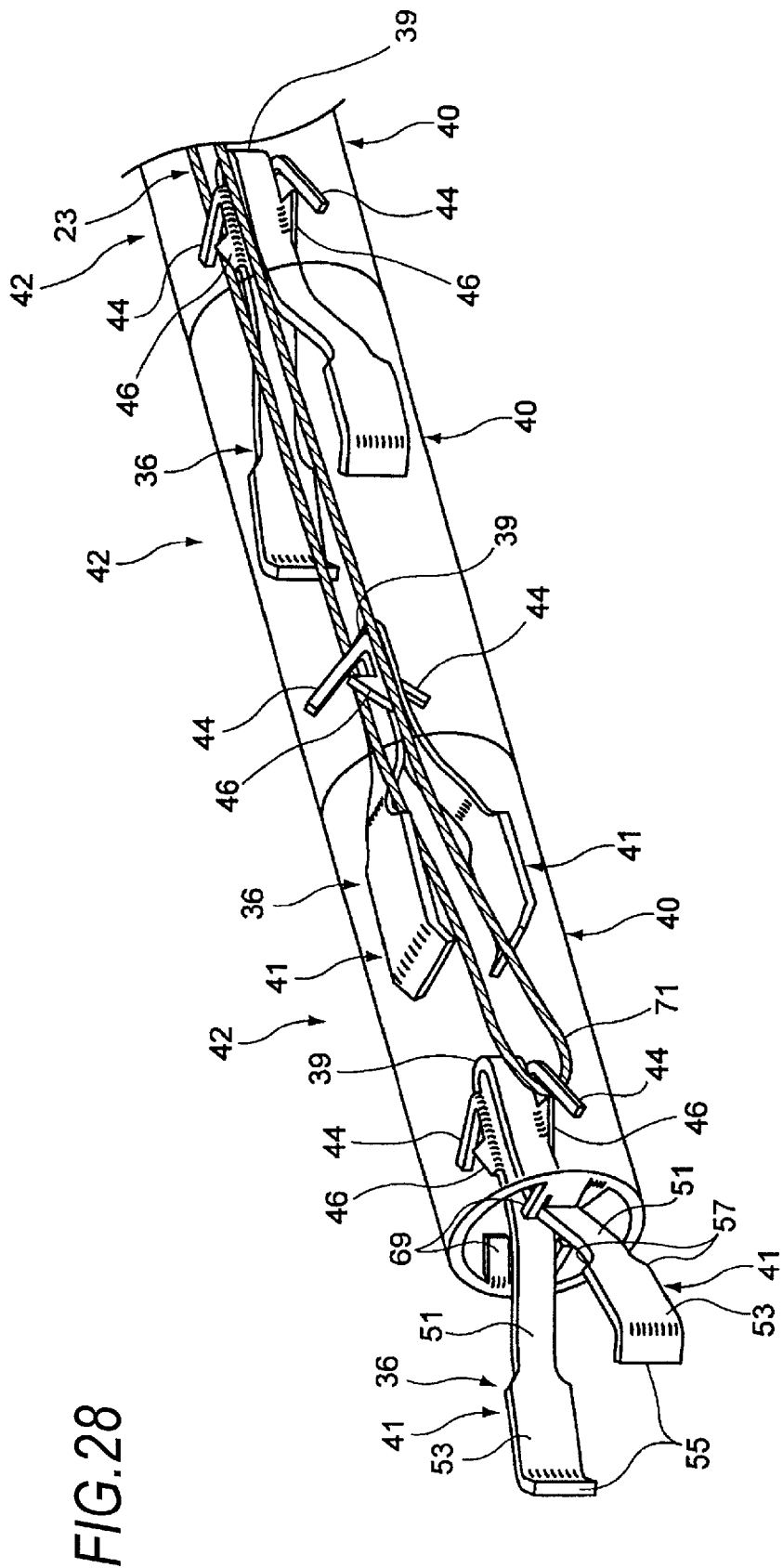
FIG. 28 is a perspective view illustrating a state where a plurality of clip units are disposed in a line with the enlarged opened direction of the arm parts of the clip units being different alternately by 90 degrees.
Figure 29:
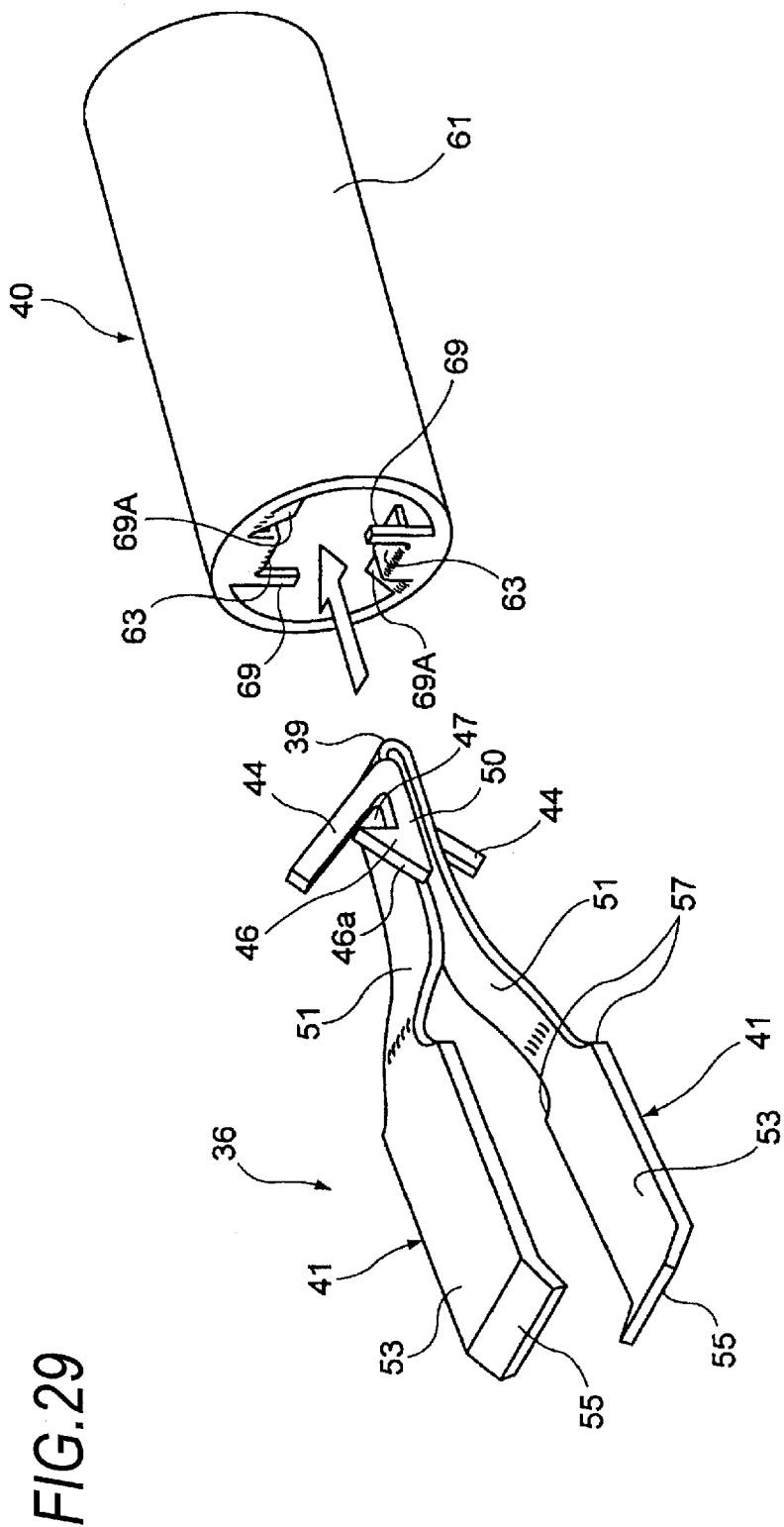
FIG. 29 is a perspective view of the fastening ring and the clip body in FIG. 28.

Next, other configuration example of a clip unit will be described. FIG. 28 is a perspective view illustrating a state where a plurality of clip units are arranged in a line while the enlarging opening direction of arm parts thereof are different by 90 degrees each other, FIG. 29 is an exploded perspective view of a clip unit, FIG. 30A is a plan view of a clip body, FIG. 30B is a front view of the clip body, and FIG. 30C is a side view of the clip body.

As illustrated in FIG. 28, in the configuration of the clip units, a plurality of clip units 42 configured such that each clip body 36 is inserted into the corresponding fastening ring 40 are alternately arranged in the axis direction, thereby being aligned in series within an outer sheath member 19 (not illustrated). The aligned clip bodies 36 are configured such that the enlarging opening directions of the arm parts 41 thereof are different by 90 degrees. Further, the fastening rings 40 are disposed with a rotation by 90 degrees As illustrated in FIGS. 29, 30A, 30B and 30C, the clip body 36 includes a base end section 39 at the insertion side to the fastening ring 40, and a pair of arm parts 41 extended from the base end section 39, and configured by bending a band shaped metallic plate member having a elastic resilience such as a stainless steel in a substantial U shape.

A pair of wire engagement units of the clip body 36 constituted by engagement claws 43 and disengagement prevention parts 46 are configured such that parallel parts 50 extended at the both side of the width direction of the base end section 39, which is perpendicular to the enlarging opening direction of the arm parts of the base end section 39, are bent into the plate thickness of the clip body 36 (the enlarging opening direction of the arm parts) and disposed on the opposite angle positions of the base end section 39.

The engagement claws 44 are formed to be extendedly inclined such that the engagement claws are widener to the outside toward the arm parts 41 at a position in the bottom part 39a side of the base end section 39 than the disengagement prevention part 46. The force required for the plastic deformation of the engagement claws 44 is a plate-shaped body having a narrow width such that the force becomes larger than the force to pull the clip body 36 into the fastening ring 40.

The disengagement prevention parts 46 are protrusions which protrude toward the engagement claws 44 from a position spaced from the engagement claws 44 toward the arm parts 41 side, and have inclined surfaces 45*a* of which protrusion height toward the engagement claws 44 gradually increases toward the insertion direction to the fastening ring 40 of the clip body 35. The engagement claws 44 and the disengagement prevention parts 46 are formed by the parallel parts 50 that is formed by being bent from the side end of the base end section 39 in the width direction. Accordingly, as illustrated in FIGS. 29 and 30A, a gap 47 to be engaged with the loop part 71 of the manipulation wire 23 is defined by the engagement claw 44, the disengagement prevention part 46, and the parallel part 50 of the base end section 39.

The force required for the plastic deformation of the engagement claws 44 is set to be larger than the force to pull the clip body 36 into the fastening ring 40. Accordingly, in the clip body 36, the manipulation wire 23 is pulled in a state where the loop part 71 of the manipulation wire 23 illustrated in FIG. 28 is engaged with the engagement claws 44, and thus, the clip body 36 may be pulled into the fastening ring 40 without plastic deformation of the engagement claws 44.

As illustrated in FIG. 29, the fastening ring 40 includes a hollow cylindrical part 61 and a pair of clip contact parts 63. Each of the pair of clip contact parts 63 includes a flat surface parallel to the axis of the fastening ring 40 by bending a protrusion protruded from an end of the cylindrical part 61, the flat surfaces contact to eh both outer surfaces of the arm parts 41 to guide the clip body 36, thereby restricting the rotation of the clip body 36 against to the central axis of the fastening ring 40.

Further, the both sides of the clip contact parts 63 are provided with a pair of guide members 69, 69A that protrude inwardly in the diameter direction of the fastening ring 40. When the clip body 36 is inserted into the fastening ring 40, the guide member 69A is formed inclined to the inner side of the ring toward the insertion direction of the clip body 36. The guide member 69A is formed in a side to which the engagement claw 44 contacts. Accordingly, when the clip body 36 is inserted into the fastening ring 40, the engagement claw 44 contacts with the inner side of the guide member 69A, thereby preventing the clip body 36 from being drawn out from the fastening ring 40. In addition, the distance of the pair of guide members 69 is smaller than the width of the wide width part 53 W2 (see, FIGS. 4A and 4B), step parts 57 between the wide width part 53 and the plate-shaped member 51 contact with the pair of guide member 69, thereby limiting the insertion length of the clip body 36 into the fastening ring 40.

Then, when the step parts 57 of the clip body 36 contact with the fastening ring 40 (the pair of guide members 69) by pulling the manipulation wire 23 and pulling the clip body 36 into the fastening ring 40, the plastic deformation of the engagement claws 44 is initiated to disengage of the engagement claws 44 and the loop part 71 of the manipulation wire 23. As a result, a clip unit 42 may be separated from other clip unit.

The engagement claws 44 are contacted with the inner circumference surface of the fastening ring 40 by being resiliently biased when the clip body 36 is inserted into the fastening ring 40. Further, when the manipulation wire 23 is pulled, the inclined surfaces 46*a* of the disengagement prevention parts 46 guide the loop part 71 to be surely inserted into the gap 47 for engaging the manipulation wire 23.

Other configuration and effects are the same as in the configuration examples as described above, and thus, the description thereof will be omitted.

Like this, the present invention is not limited to the above-described configuration examples. It is expected by the present invention that modifications and applications will be made by a person skilled in the art on based on the disclosure of the specification and a well-known technology, and the modifications and applications are included in the scope to be protected.

As described above, the following items are disclosed in the specification.

(1) A ligation device for ligating a biological tissue, include: a flexible tube-shaped outer sheath member; a tube-shaped inner sheath member provided within the outer sheath member to be freely reciprocated; a manipulation wire provided within the sheath member to be freely reciprocated; and a plurality of clip units disposed in series within the distal end of the outer sheath member, in which each of the clip units includes a clip body that ligates the biological tissue using a pair of arm parts biased to be largely opened each other and a base end section that connects the base ends of the arm parts, and a fastening ring configured to close the pair of arm parts by inserting the base end section of the clip body within a cylindrical body of the fastening ring, and in which the fastening ring includes: a connecting unit to connect adjacent fastening rings to each other; and a disconnection unit to engage with the manipulation and deforms the connecting unit by the pull of the manipulation wire, thereby releasing the connection of the fastening rings.

According to the ligation device, since the adjacent fastening rings are connected with each other by the connecting unit, the connecting unit is deformed by the pulling of the manipulation wire, and thus, the biological tissues may be sequentially ligated using the plurality of clip units without generating fragments.

(2) In the ligation device of (1), the manipulation wire includes a loop part at the front end of the manipulation wire, and the connecting unit of the fastening ring includes: a locking member extended from one fastening ring toward the other fastening ring and including a first fitting part at the front end thereof; and a second fitting part formed in a part of the other fastening ring and fitted with the first fitting part.

According to the ligation device, since the connecting unit of the fastening rings includes the first fitting part formed in one fastening ring and the second fitting part formed in the other fastening ring to be fitted with the first fitting part, the adjacent fastening rings may be surely connected with each other.

(3) In the ligation device of (2), the disconnection unit includes a wire engagement member extended from a part of the locking member to engage with the loop part of the manipulation wire.

According to the ligation device, since the connection of the fastening rings is released by the wire engagement member extended from a part of the locking member and configured to be engaged with the loop part of the manipulation wire, the connection of the fastening rings may be automatically released by the pull of the manipulation wire.

(4) In the ligation device of (2), the disconnection unit includes: protrusions protruded from the base end section of the clip body in a direction perpendicular to the longitudinal direction of the clip; a diameter reducing part formed in a part of the fastening ring and configured to abut against the protrusions when the clip body is inserted into the fastening ring; and diameter enlarging slits cut-off from a end opposite to the clip body-insertion side of the fastening ring up to a place beyond the diameter reducing part along the axis direction.

According to the ligation device, since the disconnection unit includes the protrusions protruded at the base end section of the clip body, the diameter reducing part of the fastening ring in which the protrusion contacts thereto, and the diameter enlarging slit formed by cutting off the fastening along the axis direction, the connection of the fastening rings may be released by contacting the protrusion with the diameter reducing part to press the fastening ring to the outside.

(5) In the ligation device of (4), the diameter enlarging slits are formed in plural of circumference positions against the arranging positions of the connecting unit of the fastening ring.

According to the ligation device, since the diameter enlarging slits are formed in the plurality of circumference positions over the arrangement positions of the connecting unit, the connection of the fastening rings may be surely released.

(6) The ligation device of any one of (1) to (5), further includes: a wire engagement part formed in the base end section of the clip body and configured to engage with the loop part of the manipulation wire, in which the wire engagement part includes: engagement claw configured to be inclined and extended from the base end section of the clip body toward the rear side in a direction where fastening ring is inserted; and disengagement prevention part configured to prevent the loop part of the manipulation wire engaged with the engagement claw from being drawn out from the engagement claw.

According to the ligation device, since the relative positions of the clip body and the fastening ring may be changed by bringing-up and pulling of the manipulation wire when the biological tissue is ligated, the opening/closing manipulations of the clip may be freely performed to grasp the tissue with a simple manipulation. Further, since the clip body and the manipulation wire are separated from each other by the deformation of the engagement claws of the clip body, the fragments are not generated when being separated. Therefore, there is no concern that the fragments affect to the biological tissue or the fragments disturb the ligation manipulation.

(7) In the ligation device of any one of (1) to (6), the disengagement prevention part is configured to include a protrusion protruded toward the engagement claw at a place spaced toward the arm parts than the connecting position with the engagement claw at the base end section of the clip body and define a gap to accommodate the loop part of the manipulation wire between the engagement claw.

According to the ligation device, even though the manipulation wire is maintained within the gap that engages with the loop part in a state where the wire is engaged with the gap and the manipulation wire is pulled, it is prevented that the manipulation wire is brought up from the clip body by the protrusion. Accordingly, the clip body may be surely and stably reciprocated, thereby grasping the tissue smoothly.

(8) In the ligation device of any one of (1) to (7), the contact surfaces of the end surfaces of the fastening rings are formed in a circular arc when viewed from a direction perpendicular to the axis direction of the fastening ring, and the fastening rings are freely bent within a plane parallel to the axis direction.

According to the ligation device, since the contact surfaces of the end surfaces of the adjacent fastening rings are formed in a circular arc shape, respectively, the respective fastening rings may be inclined from the arrangement where the fastening rings are arranged in a straight line to the arrangement where the rings are bent each other. Accordingly, the flexibility of the ligation device is improved, and the curve maneuverability when being inserted into the body cavity and the shape-following performance for the pipe line within the body cavity are improved.

(9) Clip units are used in a ligation device described in any one of (1) to (8).

According to the clip units, the clip unit may grasp the biological tissue, and the biological tissues may be sequentially ligated by the plurality of clip units.

INDUSTRIAL APPLICABILITY

According to the present invention, a ligation device and a clip unit used therein may be provided. While arm parts of a clip body disposed in a front end of a sheath may be freely opened/closed to grip a biological tissue among a plurality of clip units disposed in series within the sheath, the biological tissues may be sequentially ligated by the plurality of clip units without generating the fragment.

The present application is based on a Japanese Patent Application (JP 2010-212892) filed on Sep. 22, 2010, and the disclosure of which is incorporated herein in its entirety by reference.

REFERENCE SIGNS LIST 13, 14, 42, 113: Clip unit
19: Outer sheath member
21: Inner sheath member
23: Manipulation wire
35, 36, 117: Clip body
37, 38, 40, 115: Fastening ring
37b, 37c: Contact surface
39: Base end section
41: Arm parts
43, 44: Engagement claws (wire engagement part)
45, 46: Disengagement prevention part (wire engagement part)
47: Gap
71: Loop part
81: Biological tissue
87: Locking member
91, 111, 133: Support shaft (first fitting part, connecting unit)
93: Wire engagement member (disconnection unit)
100: Ligation device
101: Fitting support
103, 129: Engagement hole (second fitting part, connecting unit)
121: Diameter reducing part
127: Diameter enlarging slit
135: Protrusion (disconnection unit)

The invention claimed is:
1. A ligation device for ligating a biological tissue, comprising:
a flexible tube-shaped outer sheath member;
a tube-shaped inner sheath member provided within the outer sheath member to be freely reciprocated;
a manipulation wire provided within the sheath member to be freely reciprocated; and
a plurality of clip units disposed in series within the distal end of the outer sheath member,
wherein each of the clip units includes a clip body that ligates the biological tissue using a pair of arm parts biased to be largely opened each other and a base end section that connects the base ends of the arm parts, and
a plurality of fastening rings each of which is configured to close the pair of arm parts by inserting the base end section of the clip body within a cylindrical body of each fastening ring, wherein a fastening ring of the plurality of fastening rings includes:
- a connecting unit to connect adjacent fastening rings to each other; and
- a disconnection unit to engage with the manipulation wire and deforms the connecting unit by the pull of the manipulation wire, thereby releasing the connection of the fastening rings.

2. The ligation device of claim 1, wherein the manipulation wire includes a loop part at the front end of the manipulation wire, and the connecting unit of the fastening ring includes:
- a locking member extended from one fastening ring toward the other fastening ring and including a first fitting part at the front end thereof; and
- a second fitting part formed in a part of the other fastening ring and fitted with the first fitting part.

3. The ligation device of claim 2, wherein the disconnection unit includes a wire engagement member extended from a part of the locking member to engage with the loop part of the manipulation wire.

4. The ligation device of claim 2, wherein the disconnection unit includes:
- protrusions protruded from the base end section of the clip body in a direction perpendicular to the longitudinal direction of the clip;
- a diameter reducing part formed in a part of the fastening ring and configured to abut against the protrusions when the clip body is inserted into the fastening ring; and
- diameter enlarging slits cut-off from a end opposite to the clip body-insertion side of the fastening ring up to a place beyond the diameter reducing part along the axis direction.

5. The ligation device of claim 4, wherein the diameter enlarging slits are formed in plural of circumference positions against the arranging positions of the connecting unit of the fastening ring.

6. The ligation device of claim 1, further comprising:
- a wire engagement part formed in the base end section of the clip body and configured to engage with the loop part of the manipulation wire, wherein the wire engagement part includes:
- engagement claw configured to be inclined and extended from the base end section of the clip body toward the rear side in a direction where fastening ring is inserted; and
- disengagement prevention part configured to prevent the loop part of the manipulation wire engaged with the engagement claw from being drawn out from the engagement claw.

7. The ligation device of claim 1, wherein the disengagement prevention part is configured to include a protrusion protruded toward the engagement claw at a place spaced toward the arm parts than the connecting position with the engagement claw at the base end section of the clip body and define a gap to accommodate the loop part of the manipulation wire between the engagement claw.

8. The ligation device of claim 1, wherein the contact surfaces of the end surfaces of the fastening rings are formed in a circular arc when viewed from a direction perpendicular to the axis direction of the fastening ring, and the fastening rings are freely bent within a plane parallel to the axis direction.

\* \* \* \* \*